US012778767B1

(12) United States Patent
Cox

(10) Patent No.: US 12,778,767 B1
(45) Date of Patent: Nov. 3, 2026

(54) VARIABLE ANGLE EXPANSION MECHANISM

(71) Applicant: GLOBUS MEDICAL, INC., Audubon, PA (US)

(72) Inventor: Shawn Cox, Shrewsbury, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 19/223,369

(22) Filed: May 30, 2025

(51) Int. Cl.
*A61F 2/44* (2006.01)
*A61F 2/46* (2006.01)

(52) U.S. Cl.
CPC .......... *A61F 2/4425* (2013.01); *A61F 2/4465* (2013.01); *A61F 2/4611* (2013.01); *A61F 2220/0041* (2013.01); *A61F 2220/0091* (2013.01)

(58) Field of Classification Search
CPC ..................... A61F 2002/30538; A61F 2/4455
See application file for complete search history.

(56) References Cited

U.S. PATENT DOCUMENTS

| | | | | |
|---|---|---|---|---|
| 12,336,917 | B2 * | 6/2025 | Lauf | A61F 2/4611 |
| 12,527,671 | B2 * | 1/2026 | Weiman | A61F 2/4465 |
| 2014/0249628 | A1 * | 9/2014 | Weiman | A61F 2/4425 623/17.15 |
| 2014/0249631 | A1 * | 9/2014 | Weiman | A61F 2/447 623/17.16 |
| 2014/0249632 | A1 * | 9/2014 | Weiman | A61F 2/447 623/17.16 |
| 2016/0095718 | A1 * | 4/2016 | Burkhardt | A61F 2/4455 623/17.16 |
| 2017/0014239 | A1 * | 1/2017 | Seifert | A61F 2/4455 |
| 2017/0014240 | A1 * | 1/2017 | Seifert | A61F 2/4455 |
| 2017/0014244 | A1 * | 1/2017 | Seifert | A61F 2/30771 |
| 2017/0189200 | A1 * | 7/2017 | Miller | A61F 2/447 |
| 2017/0348116 | A1 * | 12/2017 | Weiman | A61F 2/4465 |
| 2018/0185163 | A1 * | 7/2018 | Weiman | A61F 2/442 |
| 2018/0289506 | A1 * | 10/2018 | Kim | A61F 2/4465 |
| 2018/0325693 | A1 * | 11/2018 | Weiman | A61F 2/4465 |
| 2019/0046330 | A1 * | 2/2019 | Miccio | A61L 31/146 |
| 2019/0290448 | A1 * | 9/2019 | Predick | A61F 2/447 |
| 2019/0328540 | A1 * | 10/2019 | Seifert | A61F 2/4611 |
| 2019/0380843 | A1 * | 12/2019 | Kim | A61F 2/4611 |
| 2020/0352740 | A1 * | 11/2020 | Vazifehdan | A61F 2/4455 |
| 2021/0015627 | A1 * | 1/2021 | Weiman | A61F 2/4455 |
| 2021/0113349 | A1 * | 4/2021 | Weiman | A61F 2/4465 |
| 2021/0128315 | A1 * | 5/2021 | Predick | A61F 2/447 |
| 2021/0353428 | A1 * | 11/2021 | Predick | A61F 2/447 |
| 2022/0265440 | A1 * | 8/2022 | Lauf | A61F 2/4611 |

(Continued)

FOREIGN PATENT DOCUMENTS

| | | | | |
|---|---|---|---|---|
| WO | WO-2017066226 | A1 * | 4/2017 | A61F 2/445 |

*Primary Examiner* — Jacqueline T Johanas

(57) ABSTRACT

An expanding implant that includes a lateral structure, a wedge configured to cause the lateral structure to undergo lateral movement, a captive track attached to the wedge, a pull screw that includes a captive element disposed, at least partially, within the captive track, and a pivot hinge configured to allow an implant pivot between the pull screw and the captive track, where the expanding implant is configured to undergo the implant pivot, and after the implant pivot, permit the lateral movement of the lateral structure using the pull screw.

19 Claims, 19 Drawing Sheets

(56) References Cited

U.S. PATENT DOCUMENTS

| | | | | |
|---|---|---|---|---|
| 2023/0165606 | A1* | 6/2023 | Thommen | A61F 2/4455 606/246 |
| 2023/0255788 | A1* | 8/2023 | Weiman | A61F 2/4465 623/17.16 |
| 2023/0293312 | A1* | 9/2023 | Weiman | A61F 2/447 623/17.16 |
| 2023/0372122 | A1* | 11/2023 | Martin | A61F 2/30771 |
| 2024/0277488 | A1* | 8/2024 | Semler | A61F 2/4455 |
| 2025/0099263 | A1* | 3/2025 | Seaman | A61F 2/4455 |
| 2025/0120820 | A1* | 4/2025 | Valkoun | A61F 2/447 |
| 2025/0312167 | A1* | 10/2025 | Zakelj | A61F 2/4425 |

* cited by examiner

VARIABLE ANGLE EXPANSION MECHANISM

FIELD OF INVENTION

The disclosure generally relates to surgical devices for spinal surgeries, and in particular, to an expansion mechanism used in transforaminal lumbar interbody fusion (TLIF) operations.

BACKGROUND

Devices and/or components of devices are often capable of performing certain functionalities that other devices and/or components are not configured to perform and/or are not capable of performing. In such scenarios, it may be desirable to adapt one or more systems to enhance the functionalities of devices and/or components that cannot perform the one or more functionalities.

BRIEF DESCRIPTION OF DRAWINGS

These drawings illustrate certain aspects of some examples of the present disclosure and should not be used to limit or define the disclosure.

DETAILED DESCRIPTION

Overview and Advantages

In general, this application discloses one or more embodiments of methods and systems for an expansion mechanism used for transforaminal lumbar interbody fusion (TLIF), and the insertion thereof. Specifically, as disclosed in one or more embodiments herein, Transforaminal Lumbar Interbody Fusion (TLIF) is a procedure for spinal fusion which involves a posterior approach to access the intervertebral disc space. Typically, an implant is inserted at an oblique angle (typically 15°-30° from the midline) to provide stability and facilitate fusion. Conventional TLIF mechanisms include static straight, expandable straight, static articulating, and expandable articulating devices. Articulating implants are particularly advantageous as articulating implants can be steered into a more anterior position within the disc space after insertion. This optimal positioning helps restore the natural lumbar curve (lordosis) and allows the implant to rest on the stronger apophyseal ring bone, potentially reducing the risk of subsidence (the implant sinking into the vertebral bone).

Further enhancing these benefits, expandable articulating cages offer the ability to be inserted at a minimal height, thereby reducing disruption to surrounding tissues, and then expanded to achieve a customized fit for the patient. This tailored fit can also help prevent post-operative implant migration. However, a significant challenge with existing expandable articulating TLIF implants lies in their expansion mechanism. Most expandable implants, especially straight ones, utilize a drive screw and ramp system to achieve height changes. This mechanism becomes problematic in articulating implants because their angled placement means the insertion instrument's trajectory often does not align with the longitudinal axis of the implant, where the drive screw is typically located. This misalignment makes reliably expanding the implant difficult when the implant is articulated to a desired angle.

As disclosed in one or more embodiments herein, an expanding implant is provided which may be reliably expanded to the desired height at any angle from 0° (straight) to approximately 75° (angle relative to the insertion direction and implant's longitudinal axis). To accomplish this, as detailed herein, an expanding implant may include a pivoting threaded connection, a rotary driver engaging an implant pull screw, and an internal system featuring wedge to shift lateral structures outwards. Accordingly, such an expanding implant allows for off-axis expansion, regardless of the articulation angle.

—FIGS. 1A-1H—

Figure 1A:
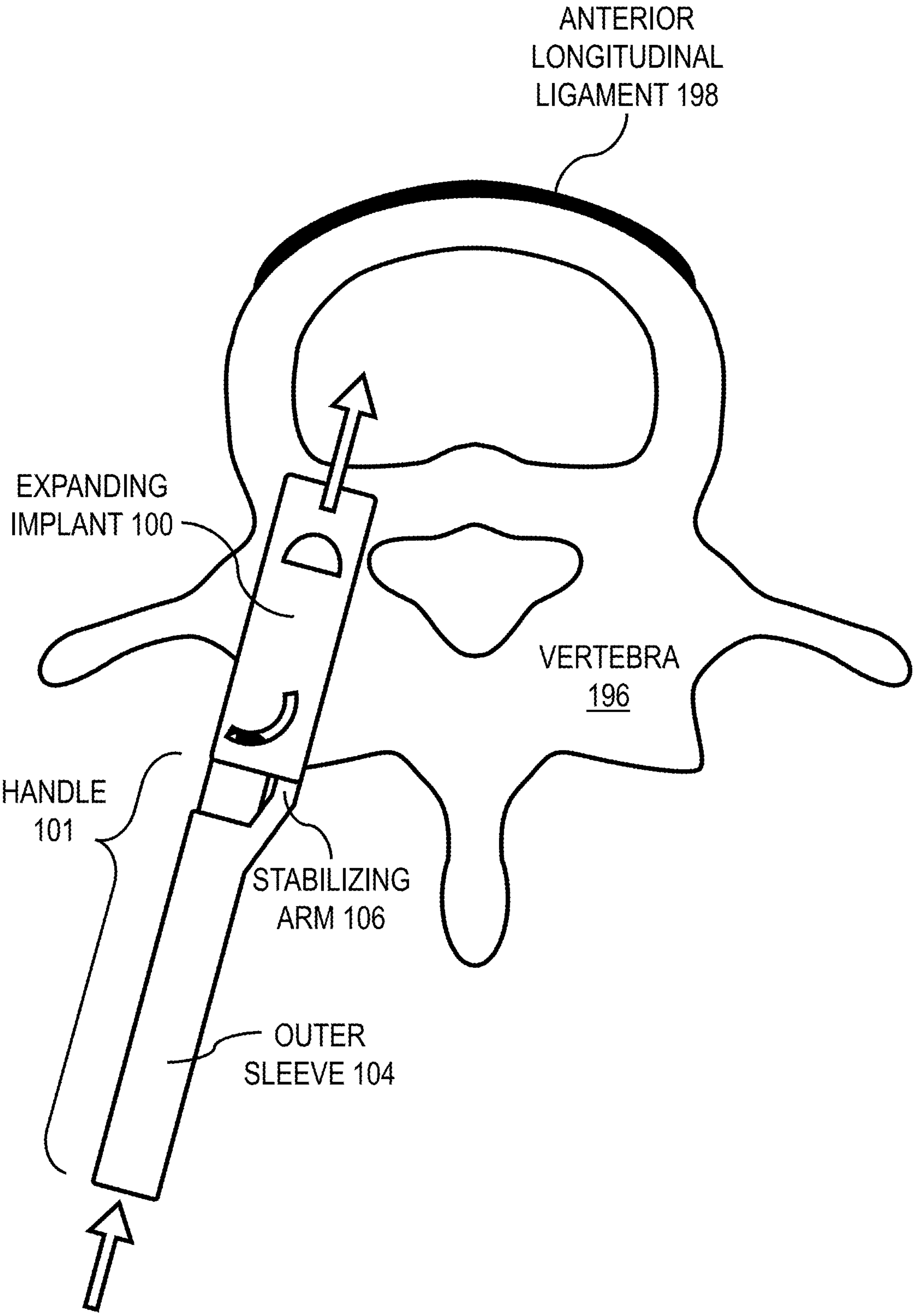
FIG. 1A is a transverse view of an expanding implant as it begins to be inserted adjacent to a vertebra.
Figure 1B:
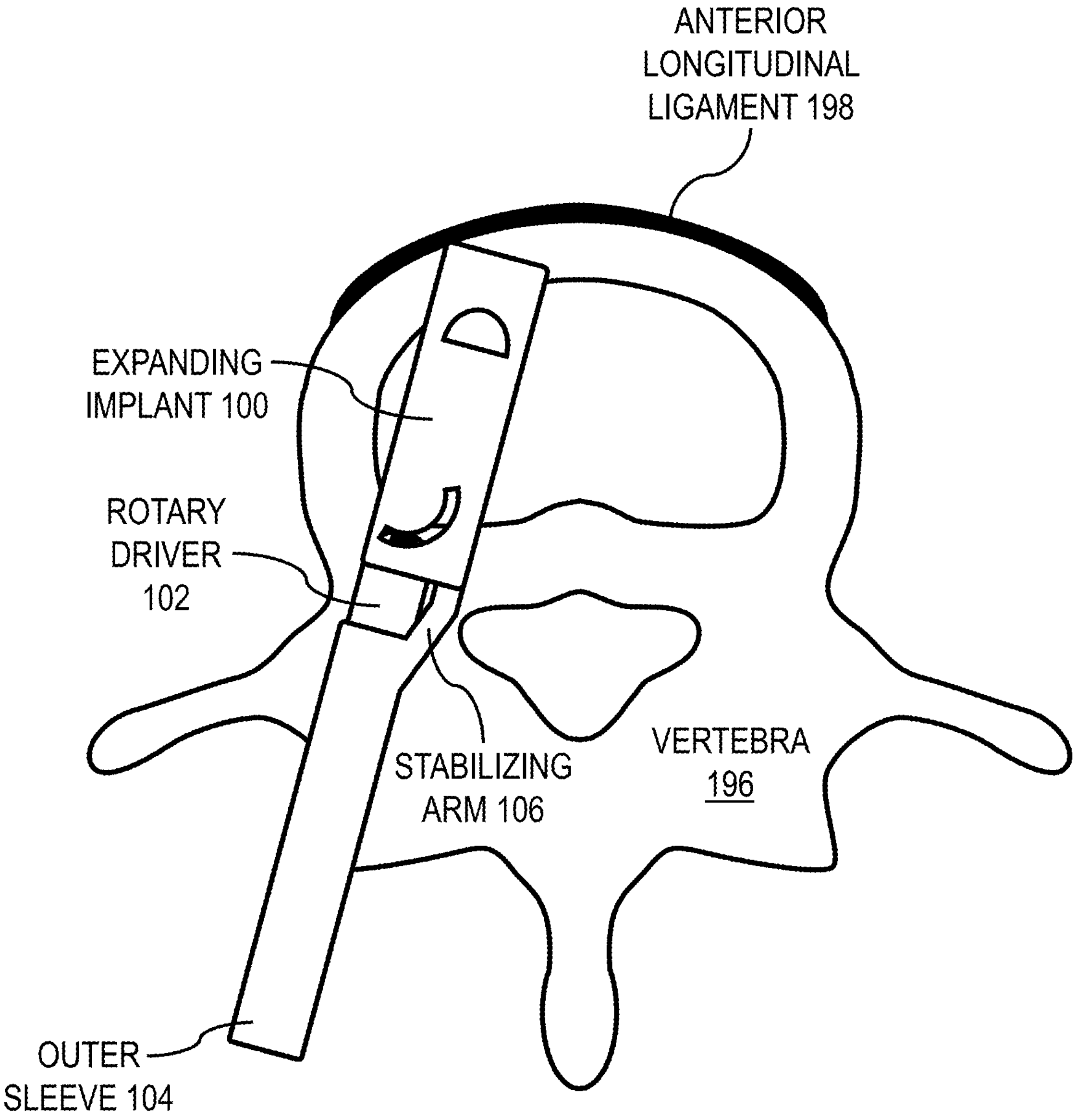
FIG. 1B is a transverse view of an expanding implant as it contacts the anterior longitudinal ligament.
Figure 1C:
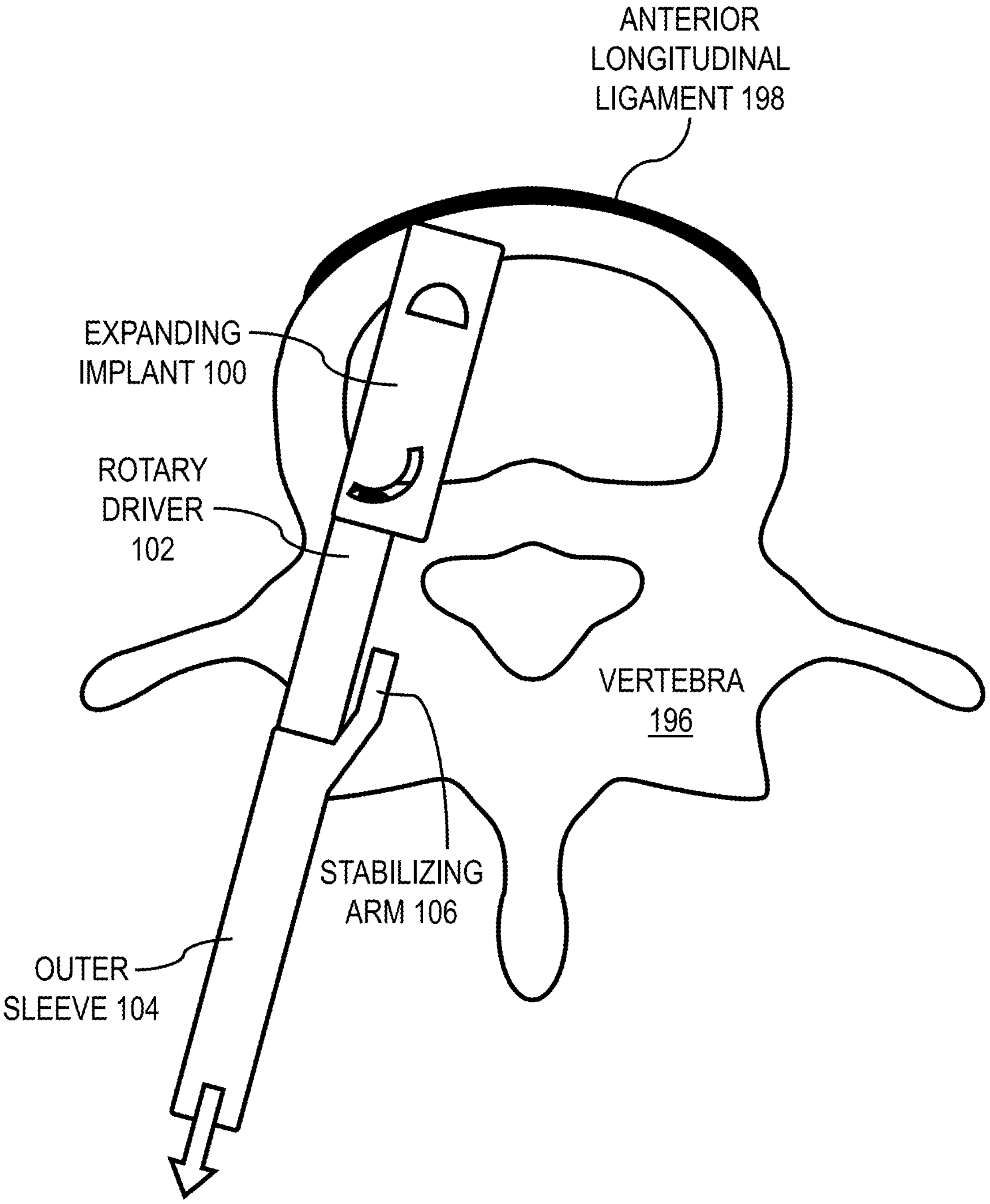
FIG. 1C is a transverse view of an expanding implant as the outer sleeve and
stabilizing arm are removed.
Figure 1D:
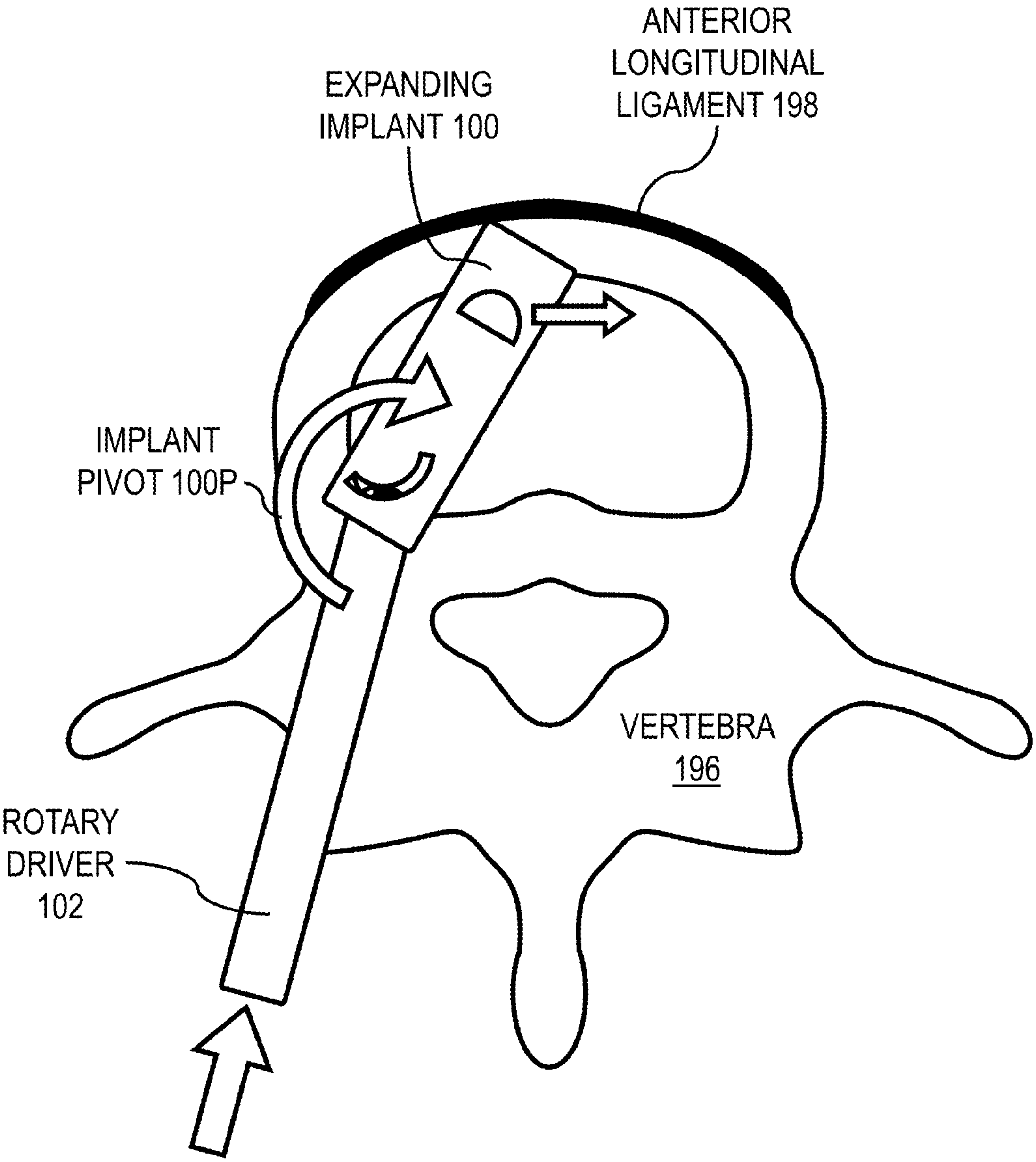
FIG. 1D is a transverse view of an expanding implant as it is inserted further and rotates.
Figure 1E:
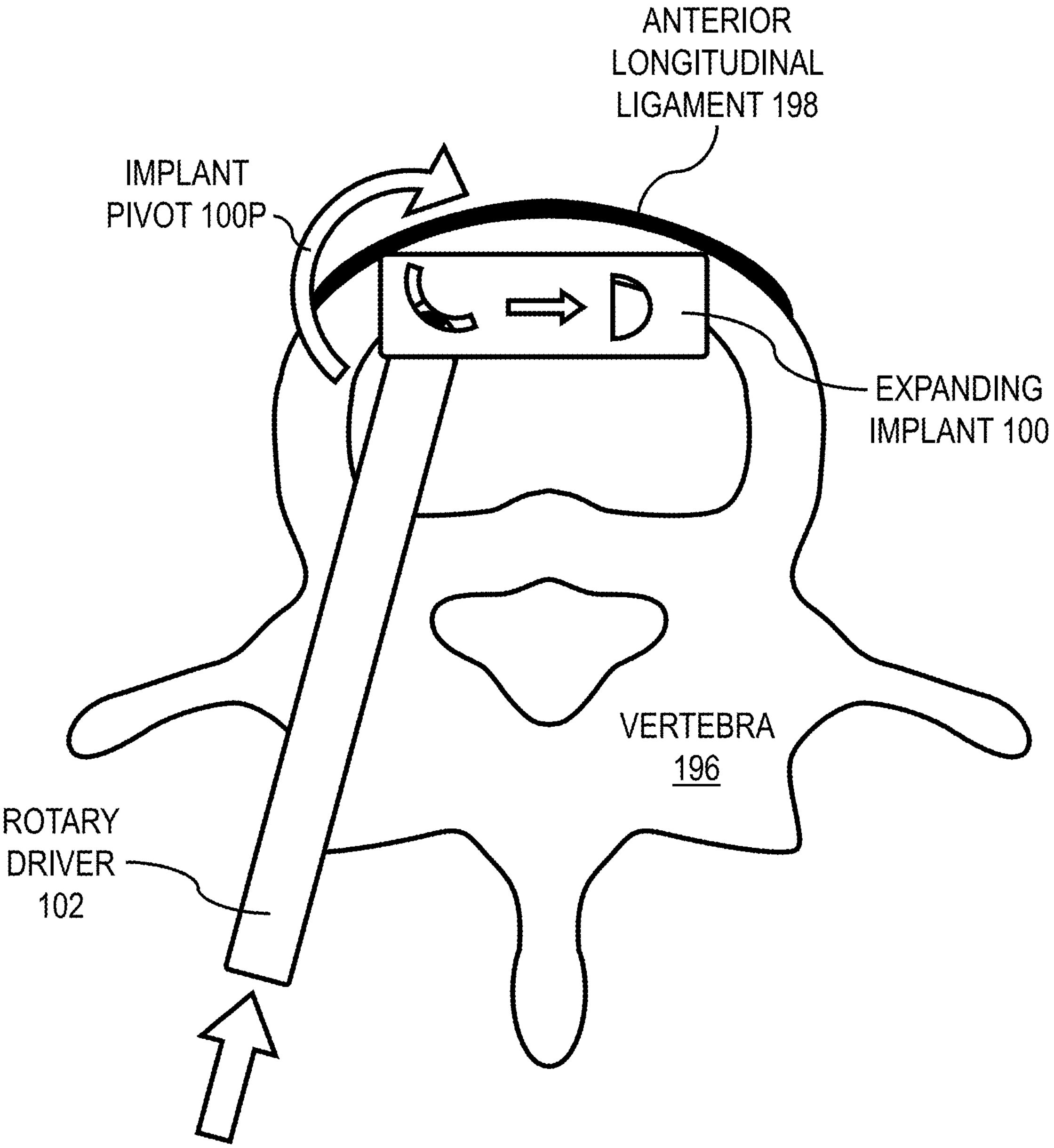
FIG. 1E is a transverse view of an expanding implant in its final position rotated against the anterior longitudinal ligament.
Figure 1F:
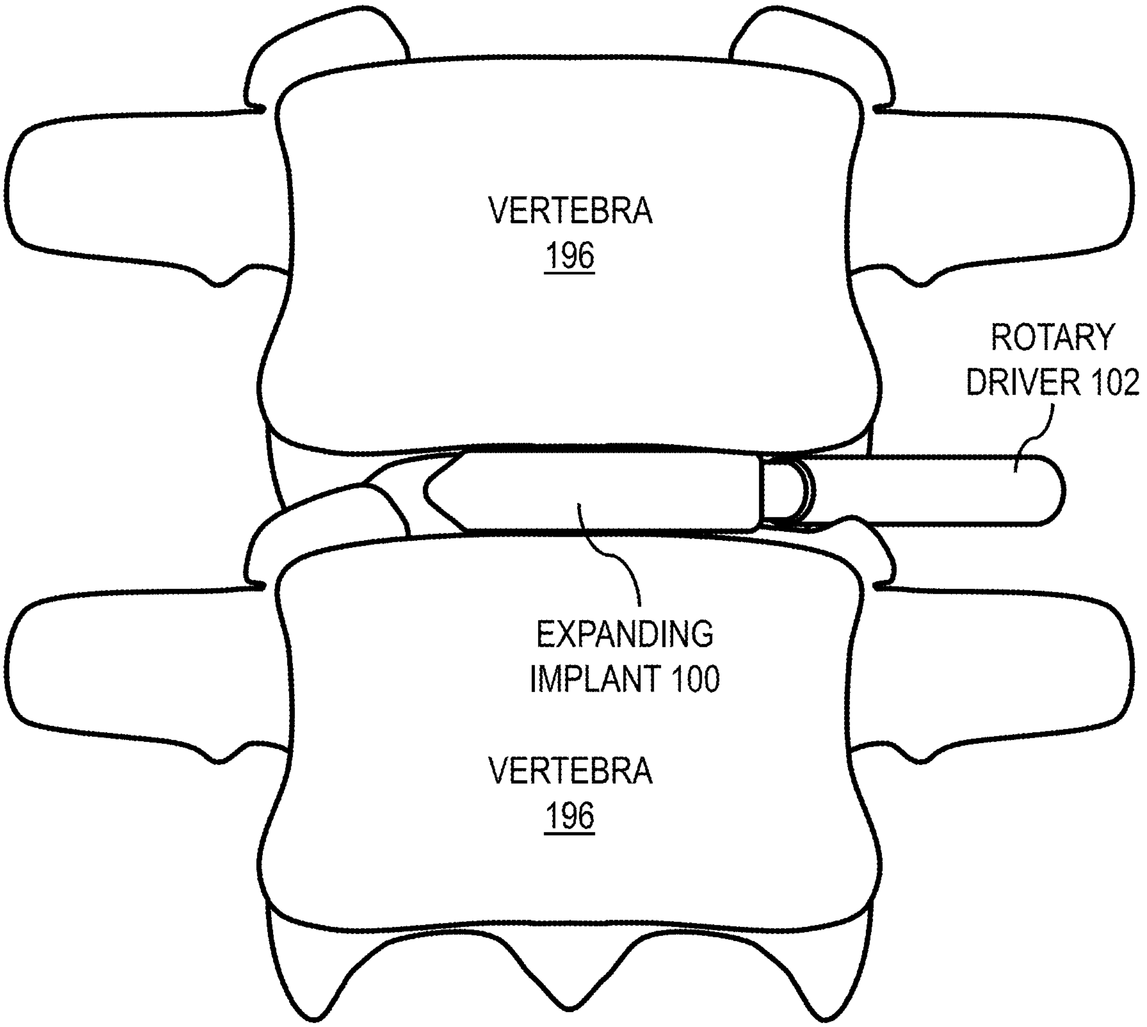
FIG. 1F is a rear coronal view of an expanding implant between two vertebrae before expansion.
Figure 1G:
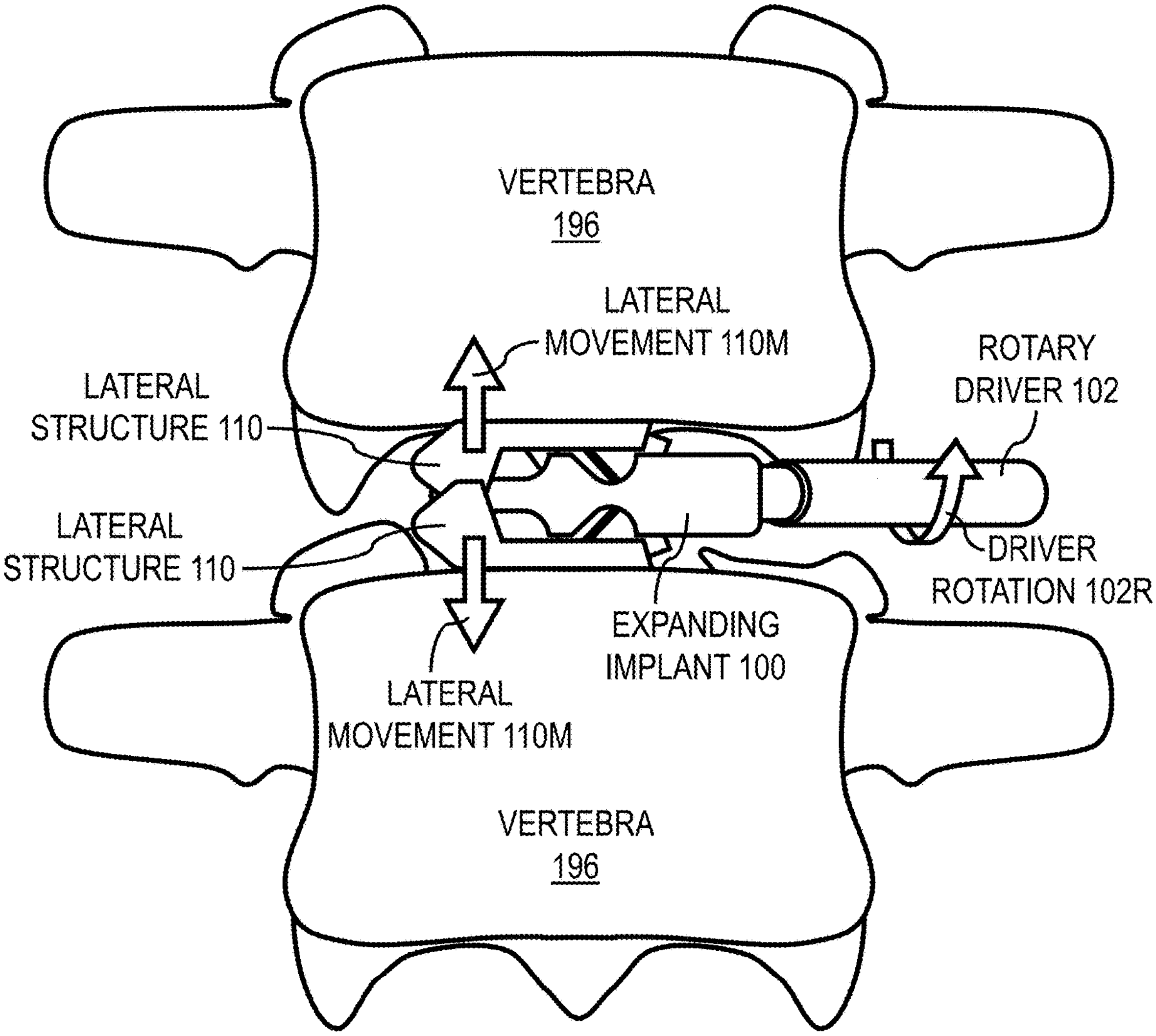
FIG. 1G is a rear coronal view of an expanding implant between two vertebrae after expansion.
Figure 1H:
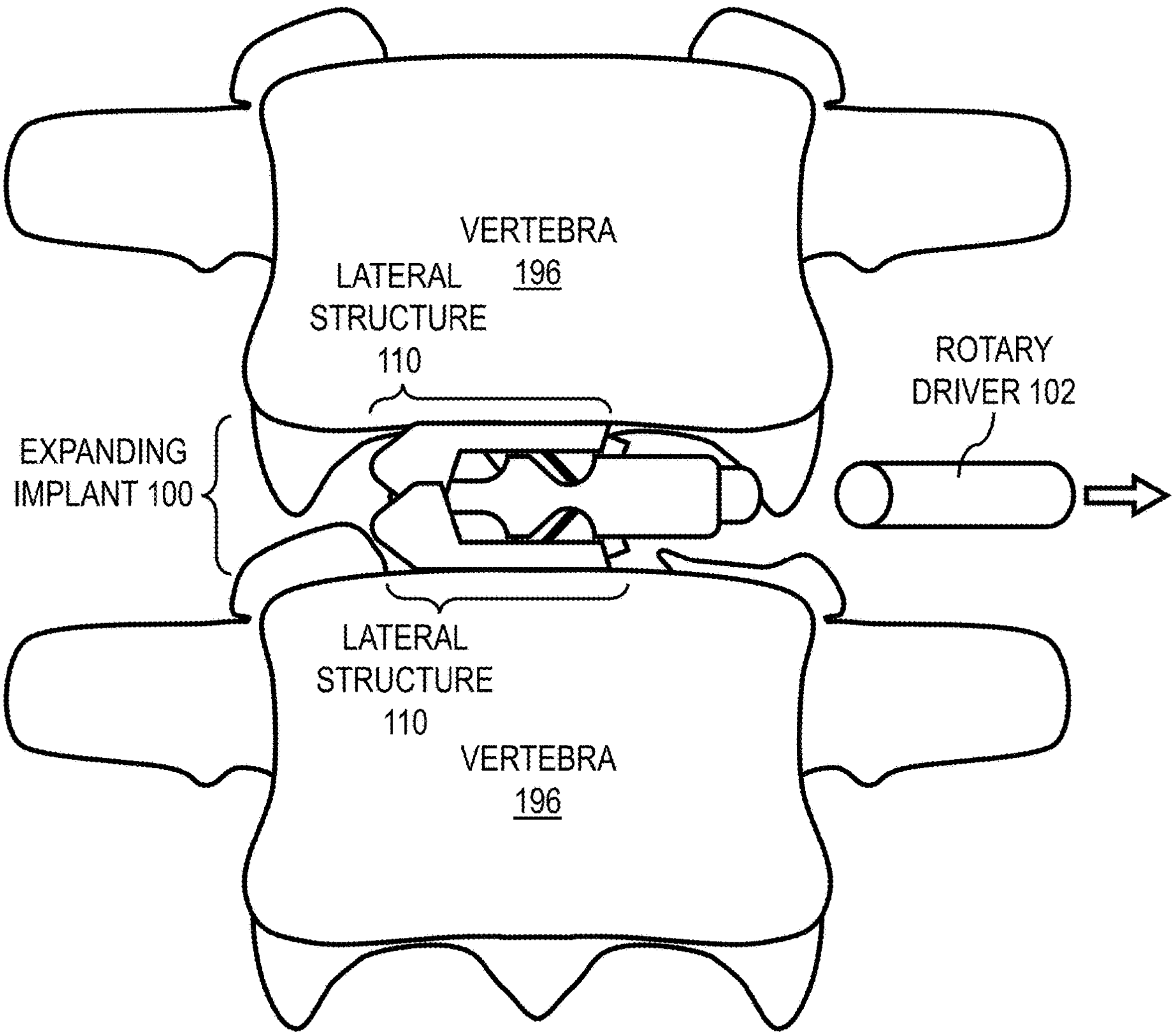
FIG. 1H is a rear coronal view of an expanding implant between two vertebrae after removal of the rotary driver.

FIG. 1A is a transverse view of an expanding implant as it begins to be inserted adjacent to a vertebra. FIG. 1B is a transverse view of an expanding implant as it contacts the anterior longitudinal ligament. FIG. 1C is a transverse view of an expanding implant as the outer sleeve and stabilizing arm are removed. FIG. 1D is a transverse view of an expanding implant as it is inserted further and rotates. FIG. 1E is a transverse view of an expanding implant in its final position rotated against the anterior longitudinal ligament. FIG. 1F is a rear coronal view of an expanding implant between two vertebrae before expansion. FIG. 1G is a rear coronal view of an expanding implant between two vertebrae after expansion. FIG. 1H is a rear coronal view of an expanding implant between two vertebrae after removal of the rotary driver.

Expanding implant 100 is a mechanical device which may be employed in a surgical procedure, such as a transforaminal lumbar interbody fusion (TLIF) operation, for the purpose of creating or maintaining a separation between adjacent vertebrae 196 prior to a fusion event. In one or more embodiments, expanding implant 100 may be constructed from biocompatible materials, such as titanium, polyether ether ketone (PEEK), or a combination thereof, and may feature a mechanism for controlled expansion once positioned within an intervertebral space. This expansion can be facilitated by the one or more lateral structures 110, which are designed to exert an outwardly directed force to separate vertebrae 196 and potentially restore disc height. Furthermore, surfaces of expanding implant 100 might be textured or coated to promote osseointegration with the adjacent vertebral endplates, contributing to the stability of the spinal segment post-operatively.

Implant pivot 100P is the change angle between handle 101 and expanding implant 100 (i.e., between handle axis 542 and implant axis 540). In one or more embodiments, implant pivot 100P may be constrained by pivot hinge 216, which can permit a specific range of motion, a set of discrete angular positions, or a fixed angular offset between handle 101 and expanding implant 100. Implant pivot 100P may allow for adjustments in the trajectory or orientation of expanding implant 100 during its delivery or placement by handle 101. The design of implant pivot 100P can also contribute to the stability and rigidity of the connection when a desired angle is achieved, possibly through friction or a locking mechanism associated with constrained pivot hinge 216. In one or more embodiments, implant pivot 100P may be considered to be between (i) any component of handle 101 or components of expanding implant 100 rotationally fixed to handle 101 (e.g., mount 214, coupler 218, arm slot 212, and pull screw 422) and (ii) other components of expanding implant 100 which articulate with the larger portion of the mechanism (e.g., captive track 526, pull plate 528, wedge 530, and lateral structure 110).

Handle 101 is an elongated structure which may be utilized to facilitate the controlled positioning and accurate placement of an expanding implant 100. As a non-limiting example, handle 101 may be used to place expanding implant 100 within an intervertebral space between vertebrae 196 during a surgical procedure. In one or more embodiments, handle 101 may be configured to interface with expanding implant 100, and may incorporate a rotary driver 102, which can be employed to actuate a mechanism within expanding implant 100, such as its expansion. Furthermore, handle 101 can optionally comprise an inner sleeve 208, an outer sleeve 104, and a stabilizing arm 106, where stabilizing arm 106 may be coupled to or integrated with outer sleeve 104 to enhance stability or control during the surgical intervention.

Rotary driver 102 is an elongated structure, such as a rod, which can be utilized in the placement of an expanding implant 100 between vertebrae 196 or to actuate movement of one or more lateral structures 110 associated with expanding implant 100. In one or more embodiments, rotary driver 102 may be configured to interlock with a corresponding component of expanding implant 100, for example, coupler 218. This interlocking engagement, which facilitates the transmission of torque, may be established by various complementary mating structures, for instance, a key and corresponding keyway, splines, or appropriately shaped teeth. Such an arrangement ensures that rotational force applied to rotary driver 102 is effectively transferred to cause congruent rotation of the interconnected component within expanding implant 100 and thereby facilitate the deployment or adjustment of lateral structures 110.

Driver rotation 102R is a rotational movement or angular displacement that is applied to, or exhibited by, rotary driver 102. In one or more embodiments, driver rotation 102R may serve as an input for operating rotary driver 102, thereby facilitating the manipulation or actuation of an interconnected medical device, like expanding implant 100. This rotation can be initiated and controlled manually (directly or indirectly), for example, by a surgeon or other clinical personnel, and/or it may be effected through an automated or machine-operated system, potentially including a computer-controlled robotic apparatus. The specific parameters of driver rotation 102R, such as its direction (e.g., clockwise or counter-clockwise), total angular displacement, and rate of rotation, may be carefully selected and applied to achieve a precise mechanical action or therapeutic effect.

Outer sleeve 104 is a tubular structure, typically hollow, that can be positioned to circumscribe, both radially and axially, one or more internal components, such as rotary driver 102 and/or inner sleeve 208, which may be disposed within its lumen. In one or more embodiments, structural support, guidance for, or a protective conduit around the internal components may be provided by outer sleeve 104. Furthermore, outer sleeve 104 may be fixedly attached to, or integrally formed with, stabilizing arm 106, thereby constituting a combined structural unit.

Stabilizing arm 106 is an elongated feature that is formed as a projection extending from outer sleeve 104. In one or more embodiments, stabilizing arm 106 may be configured for interlocking with one or more components of expanding implant 100, such as arm slot 212. This interlocking is effectuated so that implant pivot 100P is prevented-thereby inhibiting a change in angle between handle 101 and expanding implant 100 (i.e., handle axis 542 and implant axis 540). Through the restriction or prevention of implant pivot 100P by stabilizing arm 106, a specific angular orientation between handle 101 and expanding implant 100 can be maintained during the initial insertion of expanding implant 100. The precise nature of the interlock, as may be provided by stabilizing arm 106 with, for example, arm slot 212, can be designed such that a robust connection is offered, whereby accurate deployment and positioning of expanding implant 100 can be facilitated.

Lateral structure 110 is a structural component of expanding implant 100 configured to be shifted or displaced outward as lateral movement 110M. In one or more embodiments, enablement of the outward shift of lateral structure 110 can be provided by a mechanism incorporating various mechanical arrangements (e.g., pull screw 422, captive element 524, captive track 526, pull plate 528, wedge 530, etc.) which may be driven by rotary driver 102. One or more such lateral structures 110 may be included in expanding implant 100, and these may be designed for symmetrical or asymmetrical expansion to achieve desired vertebral separation and support.

Lateral movement 110M is the displacement of lateral structure 110 in an outward direction relative to a central axis or body of expanding implant 100. In one or more embodiments, lateral movement 110M may be precisely controlled and can be effectuated by actuation of an internal mechanism within expanding implant 100. This movement is typically designed to be predominantly orthogonal to a longitudinal axis of expanding implant 100, whereby separation of adjacent vertebrae 196 can be facilitated. The extent or amplitude of lateral movement 110M can be adjustable, by which a tailored degree of separation based on surgical requirements may be allowed. Furthermore, lateral movement 110M may be engineered so that symmetrical or asymmetrical occurrence is achieved, depending on the specific design and intended clinical application of expanding implant 100.

Vertebra 196 is an anatomical bone found within the spinal column of vertebrate fauna. In one or more embodiments relevant to a biological subject, vertebra 196 may be disposed adjacent to at least one other vertebra 196, potentially on one or both sides along the spinal column, with an intervertebral disc (not shown) typically being positioned between consecutive vertebrae 196. Each vertebra 196 generally comprises a body, arches, and various other features. By these structures, articulation with adjacent vertebrae 196 may be facilitated, attachment points for muscles and ligaments may be present, and a protective canal for the spinal cord may be formed. Surfaces of vertebra 196 that interface with intervertebral discs or with medical devices, such as expanding implant 100, are commonly referred to as endplates.

Anterior longitudinal ligament 198 is a robust, longitudinally oriented band of fibrous connective tissue situated along the anterior surfaces of vertebral bodies and intervertebral discs within the spinal column. In one or more embodiments relevant to a biological subject, anterior longitudinal ligament 198 may extend from an attachment point at the base of the skull or upper cervical vertebrae down to the sacrum. This ligamentous structure can be composed of multiple layers of fibers of varying lengths, with deeper fibers typically connecting adjacent vertebrae 196 and more superficial fibers spanning several vertebral segments. In one or more embodiments, anterior longitudinal ligament 198 may be used to aid implant pivot 100P (after removal of stabilizing arm 106) by pushing expanding implant 100 against anterior longitudinal ligament 198 to force implant pivot 100P.

—FIGS. 2A-2E—

Figure 2A:
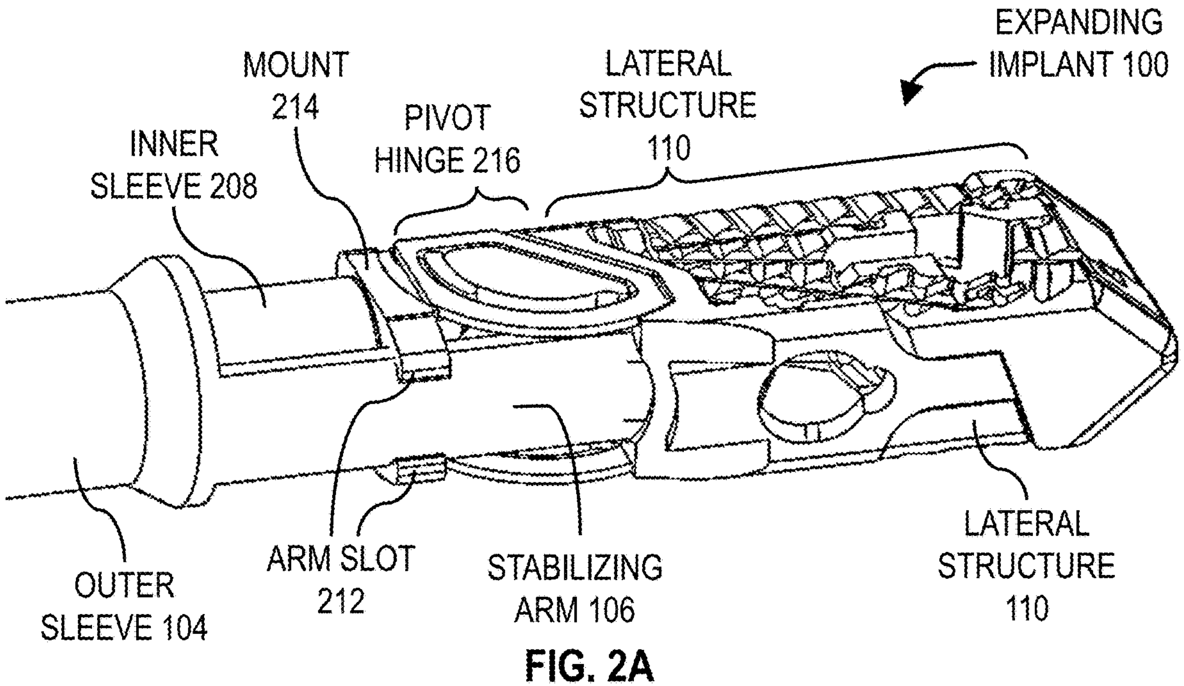
FIG. 2A is a diagram of an expanding implant with an outer sleeve and stabilizing arm attached.
Figure 2B:
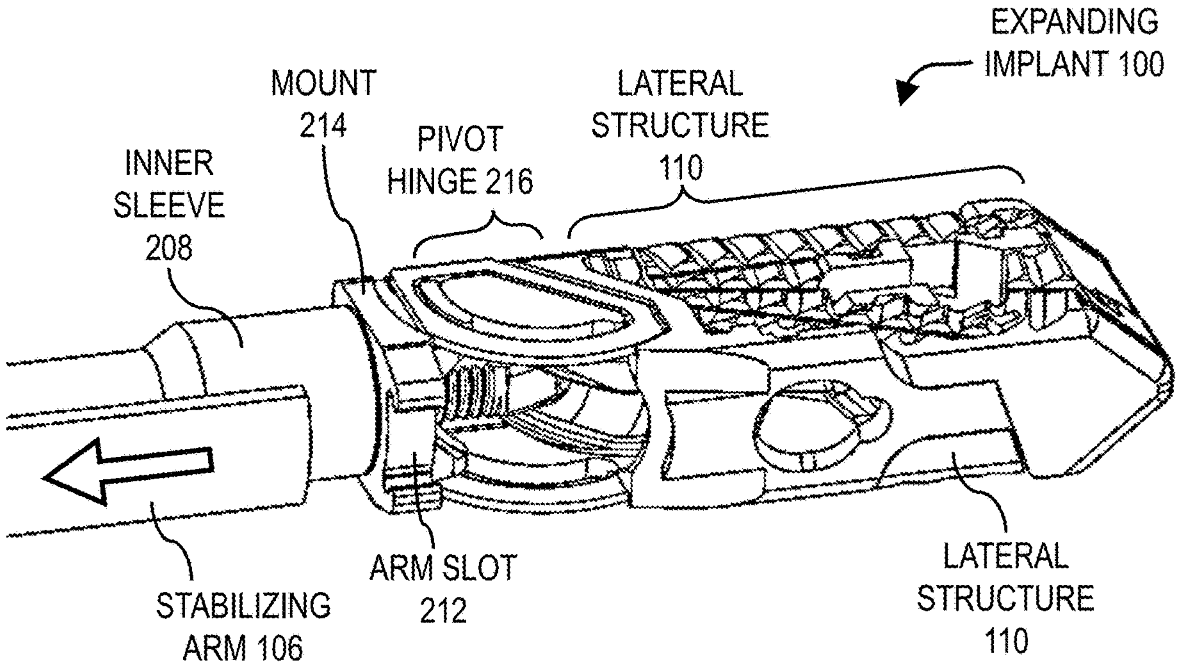
FIG. 2B is a diagram of an expanding implant showing removal of the outer sleeve and stabilizing arm.
Figure 2C:
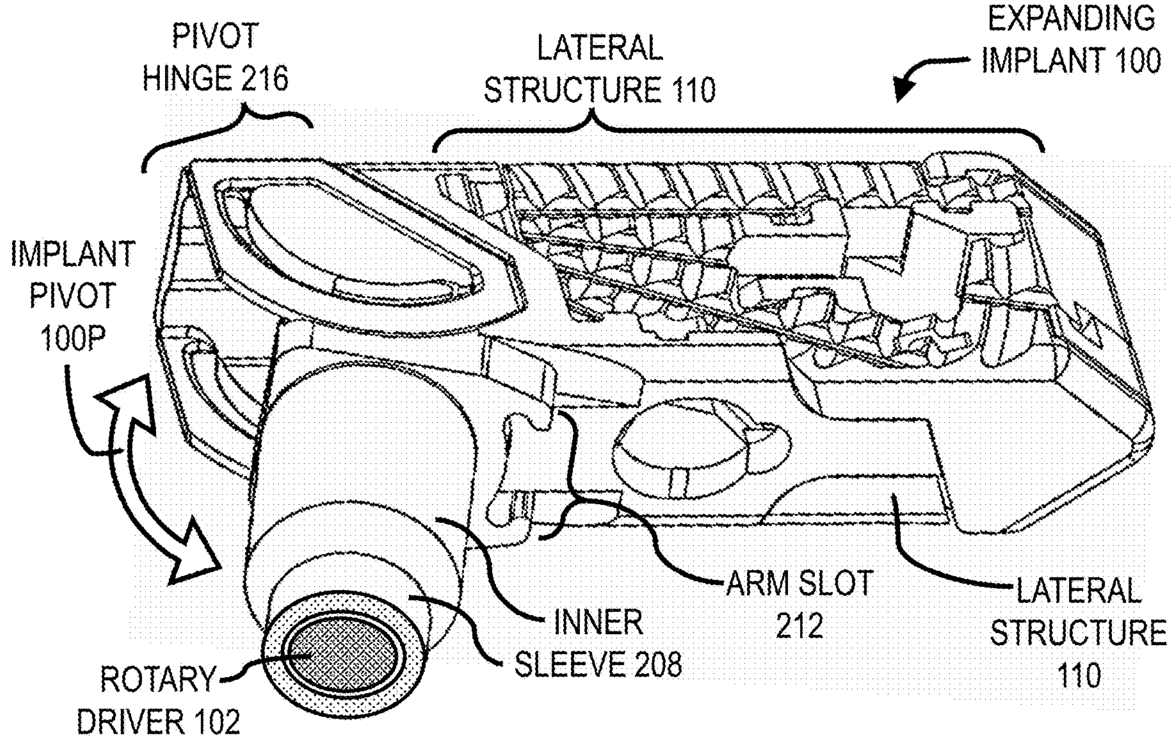
FIG. 2C is a diagram of an expanding implant after pivoting an inner sleeve and rotary driver.
Figure 2D:
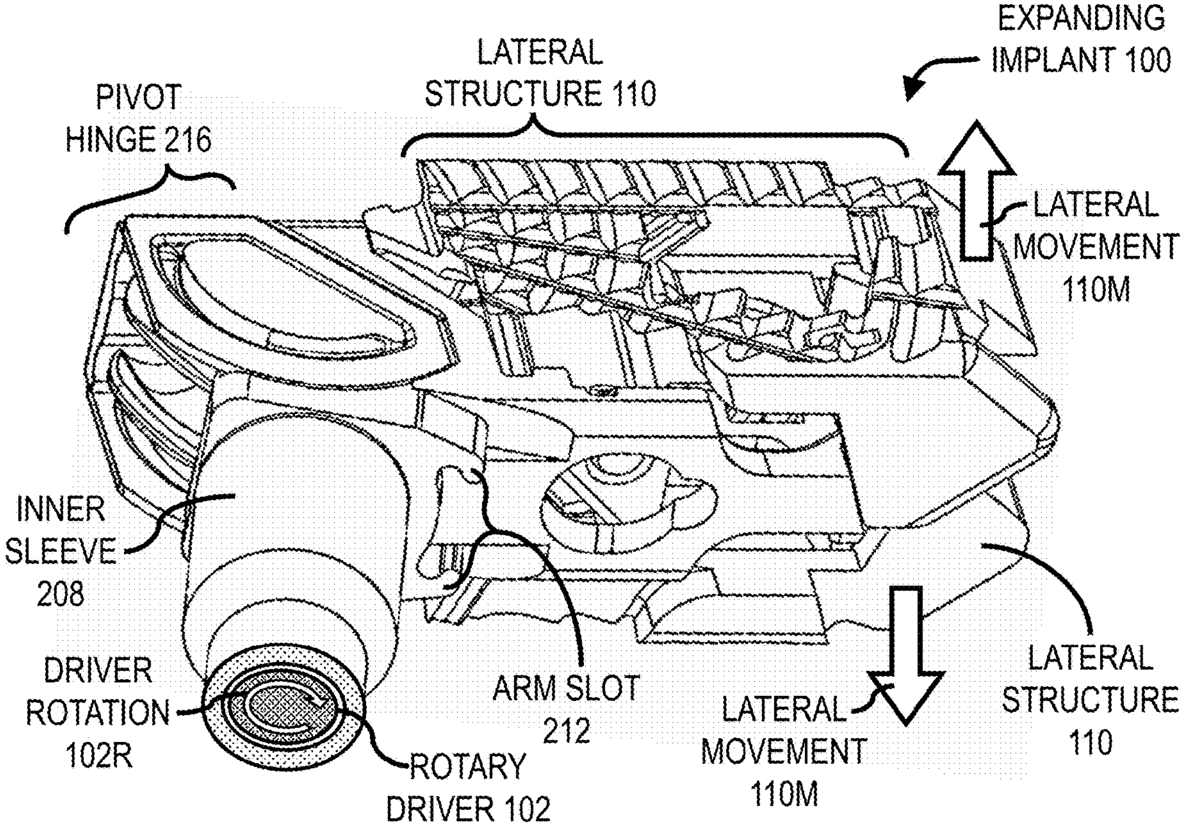
FIG. 2D is a diagram of an expanding implant showing rotation of the rotary driver to cause lateral structure movement.
Figure 2E:
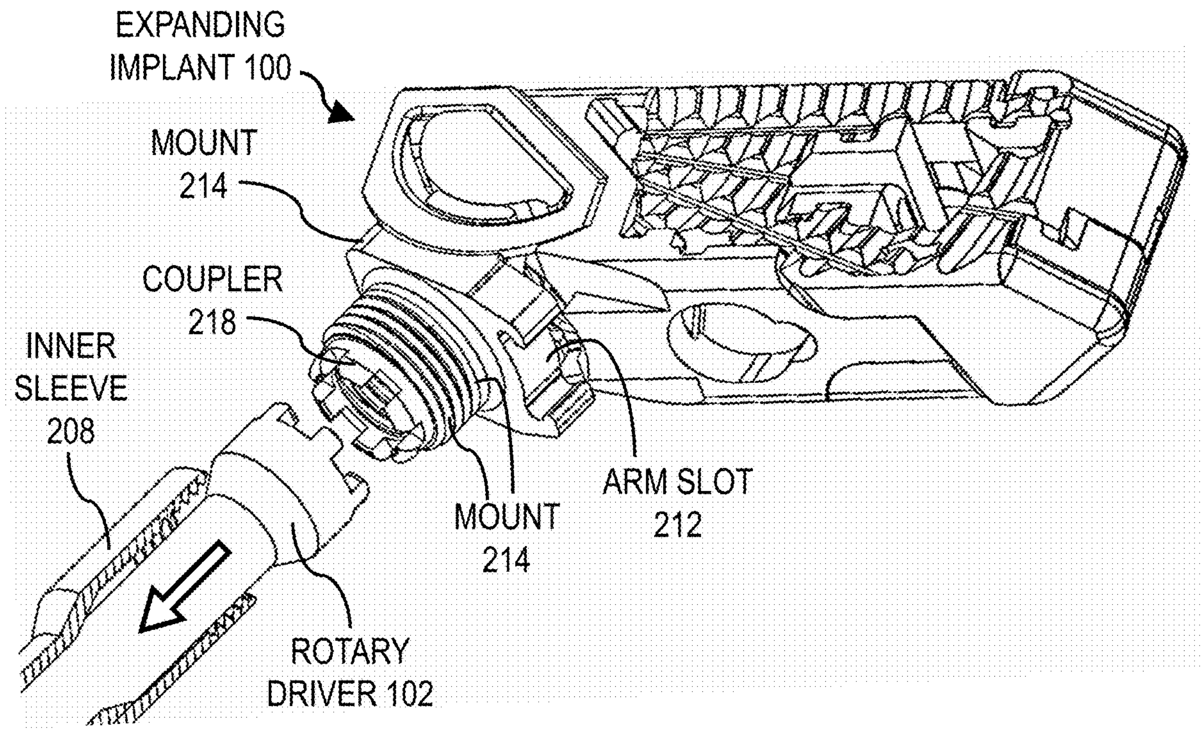
FIG. 2E is a diagram of an expanding implant showing removal of the inner sleeve and rotary driver.

FIG. 2A is a diagram of an expanding implant with an outer sleeve and stabilizing arm attached. FIG. 2B is a diagram of an expanding implant showing removal of the outer sleeve and stabilizing arm. FIG. 2C is a diagram of an expanding implant after pivoting an inner sleeve and rotary driver. FIG. 2D is a diagram of an expanding implant showing rotation of the rotary driver to cause lateral structure movement. FIG. 2E is a diagram of an expanding implant showing removal of the inner sleeve and rotary driver.

Inner sleeve 208 is a component of handle 101, which can be disposed concentrically around rotary driver 102 and situated within outer sleeve 104. In one or more embodiments, an end portion of inner sleeve 208 may be provided with threads. These threads may be designed for engagement with complementary threads on mount 214, through which a secure attachment may be facilitated. By means of such attachment, rotary driver 102 can be maintained in a predetermined position, for instance, when rotary driver 102 is interlocked with coupler 218. Additionally, formation of a barrier or a seal around rotary driver 102 may be accomplished by inner sleeve 208, whereby ingress of debris or fluids may potentially be prevented.

Arm slot 212 is a specifically configured recess or channel that is disposed on, or integrated within, mount 214. In one or more embodiments, arm slot 212 may be shaped and dimensioned for engagement and/or interlocking with stabilizing arm 106. This engagement is effectuated such that prevention of implant pivot 100P is achieved through restriction of relative movement between stabilizing arm 106 and mount 214. The geometry of arm slot 212, which can include specific contours, depths, or locking features, may be designed to ensure a secure and stable interlock with stabilizing arm 106 (e.g., stabilizing arm 106 may traverse, at least partially, through arm slot 212). Consequently, a fixed angular relationship between components associated with handle 101 and expanding implant 100 can be maintained during use.

Mount 214 is a structural component of expanding implant 100, which can be designed to serve as an interface for connection with other components, such as inner sleeve 208. In one or more embodiments, mount 214 may be provided with threads or other interlocking means for establishing engagement with inner sleeve 208. Additionally, arm slot 212 may be integrated into mount 214 or may be formed thereon. Mount 214 may include a through hole or a similar passage so that coupler 218 can be disposed therein. Further, coupler 218 may be permitted to rotate freely due to the geometry of mount 214 and coupler 218. Accordingly, rotary driver 102 may cause rotation of coupler 218 without interference from mount 214 (i.e., coupler 218 may rotate independently from mount 214).

Pivot hinge 216 is an articulating joint incorporated within expanding implant 100, which is configured to facilitate limited and constrained rotational movement. In one or more embodiments, such rotation may be enabled (by pivot hinge 216) between mount 214 (optionally fixed handle 101) and other components of expanding implant 100 (e.g., captive track 526, pull plate 528, and wedge 530). Pivot hinge 216 allows for implant pivot 100P during procedures such as placement of expanding implant 100 between two vertebrae 196. Realization of pivot hinge 216 may be achieved through any suitable hinge mechanism, including, but not limited to, a pin and track configuration or a ball joint.

Coupler 218 is a mechanical linking component through which a functional connection may be established, generally between rotary driver 102 and operational parts of expanding implant 100 (e.g., pull screw 422). In one or more embodiments, coupler 218 may be configured for interlocking with rotary driver 102, whereby torque can be received from rotary driver 102, and corresponding rotation of coupler 218 can thereby be produced. Furthermore, threads or other suitable mechanical means may be incorporated into coupler 218 so that conversion of rotational motion of coupler 218 into linear motion is achieved, which linear motion can then be imparted to pull screw 422 for actuation within expanding implant 100.

—FIG. 3—

Figure 3:
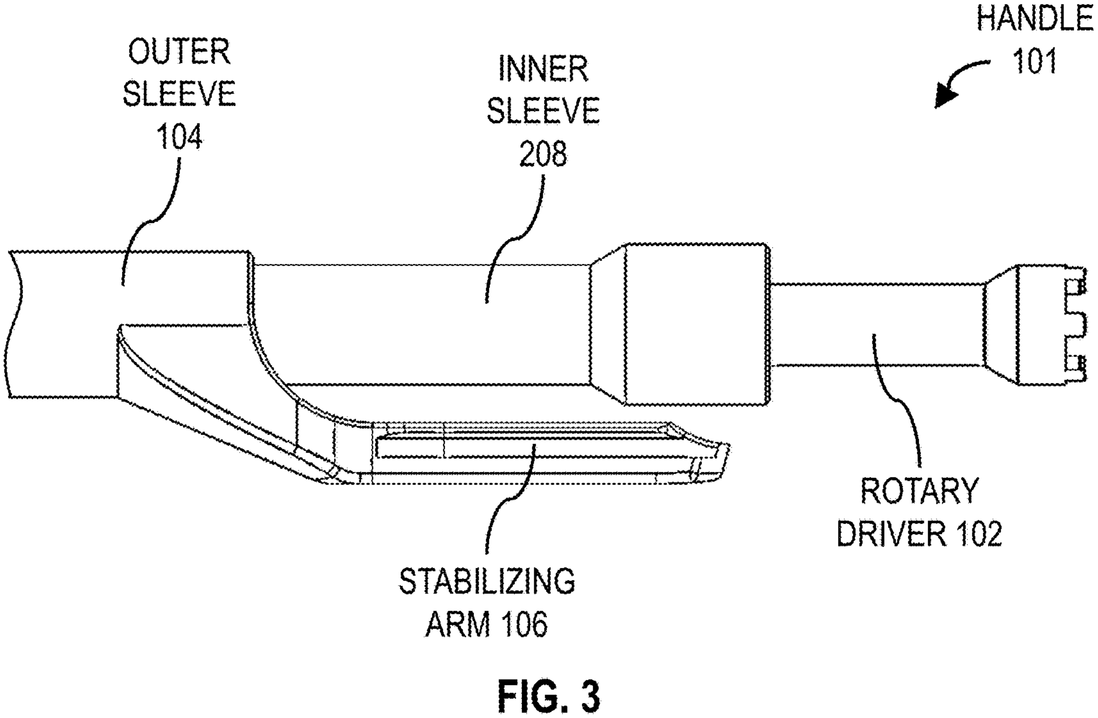
FIG. 3 is a diagram of a handle showing the assembly of an outer sleeve, inner sleeve, and rotary driver.

FIG. 3 is a diagram of a handle showing the assembly of an outer sleeve, inner sleeve, and rotary driver.

As depicted in FIG. 3, handle 101 is an assembly of components which may be configured for manual manipulation and actuation of expanding implant 100. In the illustrated example of FIG. 3, handle 101 includes outer sleeve 104 (with stabilizing arm 106), inner sleeve 208, and rotary driver 102. Each component is disposed in a specific spatial relationship to others to facilitate the intended operational characteristics of handle 101, such as controlled delivery or adjustment of expanding implant 100.

The arrangement of the handle 101 components may be configured as a telescoping assembly. In such an assembly, rotary driver 102, an elongated structure, may be partially or wholly disposed within a lumen of inner sleeve 208. Inner sleeve 208, itself being a tubular component, may be coaxially and slidably disposed within a corresponding lumen of outer sleeve 104. Due to the tubular and hollow structure, rotary driver 102 may rotate freely within inner sleeve 208 (inner sleeve 208 remaining stationary) while continuing to provide rigidity and protection to rotary driver 102.

Further, the nested or telescoping configuration permits the ordered removal of the components after the component's function is performed. For example, after expanding implant 100 reaches the most anterior point, outer sleeve 104 and stabilizing arm 106 may be removed to permit implant pivot 100P. Further, after rotary driver 102 is used to expand lateral structures 110, inner sleeve 208 may be disengaged (e.g., unthreaded) to allow for the removal of inner sleeve 208. In turn, rotary driver 102 may then be disengaged from coupler 218.

—FIGS. 4A-4B—

Figure 4A:
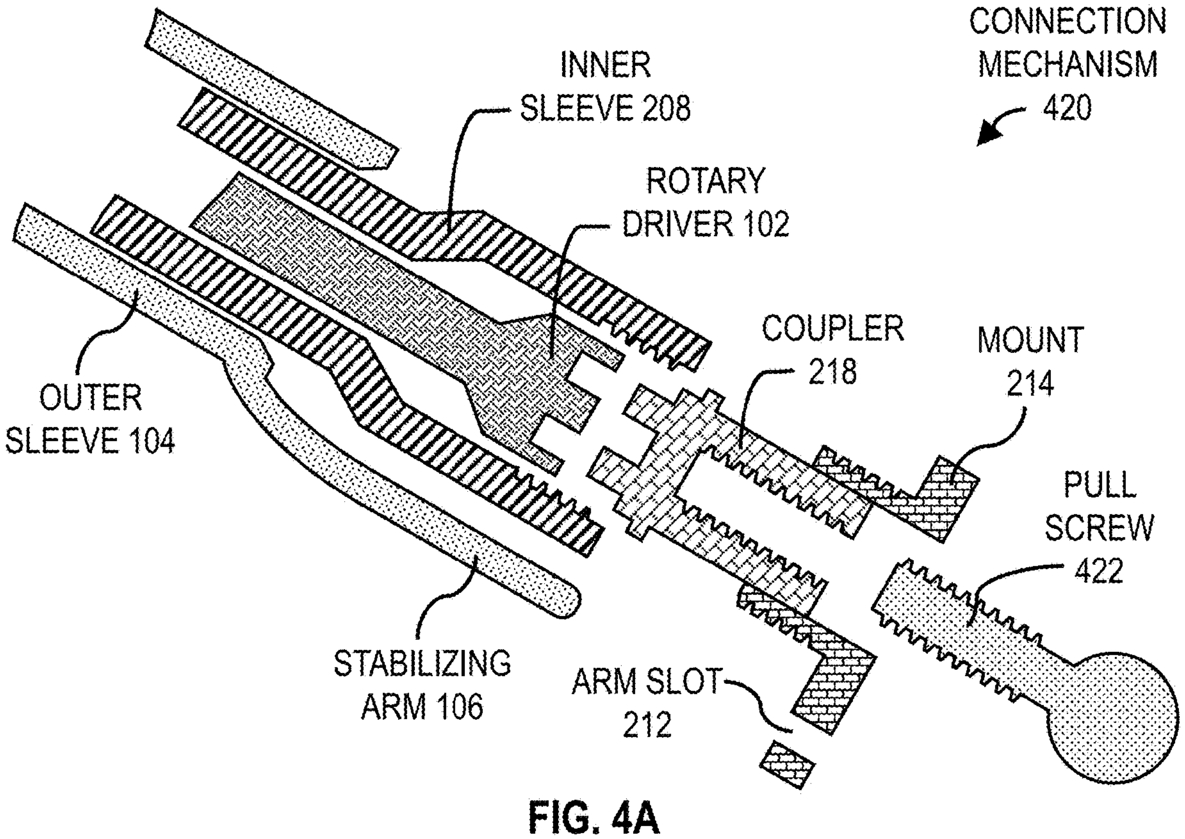
FIG. 4A is a diagram of an exploded view of a connection mechanism.
Figure 4B:
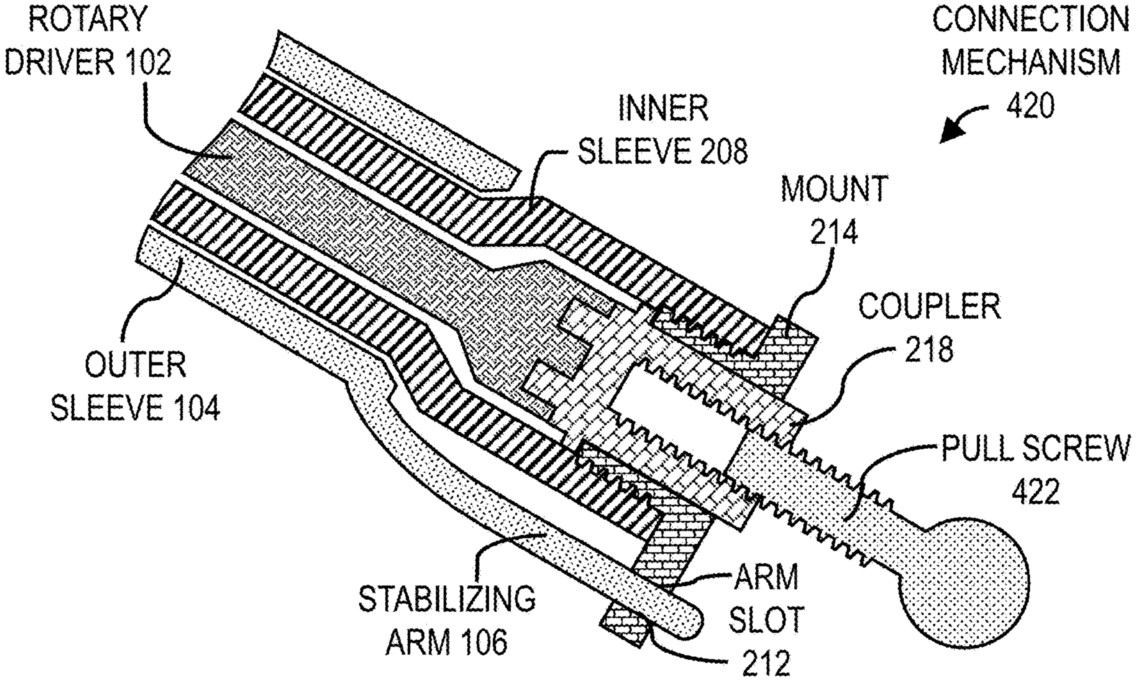
FIG. 4B is a diagram of an assembled view of a connection mechanism.

FIG. 4A is a diagram of an exploded view of a connection mechanism. FIG. 4B is a diagram of an assembled view of a connection mechanism.

Connection mechanism 420, as depicted, is a series of multiple components, which may be associated with expanding implant 100 or handle 101. Outer sleeve 104, inner sleeve 208, and rotary driver 102 are shown in a coaxial telescoping arrangement, allowing for rotation of rotary driver 102. Stabilizing arm 106, shown in proximity to or engaged with arm slot 212 on mount 214 for maintaining relative orientation or providing stability between handle 101 components and expanding implant 100.

Pull screw 422 is an elongated mechanical component of expanding implant 100. In one or more embodiments, pull screw 422 is designed to facilitate transmission of linear forces within expanding implant 100. In an embodiment, an end of pull screw 422 may be provided with threads for operative engagement with complementary threads of coupler 218. While the opposing distal end of pull screw 422 may include captive element 524. This captive element 524 may be configured to permit pivoting and limited lateral motion of pull screw 422 within captive track 526 and to enable transfer of linear motion from pull screw 422 to captive track 526, pull plate 528, and wedge 530, as may be further detailed in descriptions related to FIG. 5. Additionally, pull screw 422 may include planar cuts 632 to prevent rotation around the longitudinal axis of pull screw 422 (described in more detail with respect to FIGS. 6A-6B).

As depicted in FIG. 4B, rotary driver 102 engages with coupler 218 to permit transmission of rotation, in turn causing linear translation of pull screw 422 into coupler 218. Core operational interactions involve the transmission of motion through rotary driver 102 to coupler 218, and subsequently to pull screw 422. Rotational input, which may be initiated by manipulation of rotary driver 102, is transferred to coupler 218. This transfer can be effectuated by an interlocking engagement between distal features of rotary driver 102 and proximal features of coupler 218. Coupler 218 is shown disposed at least partially within mount 214 and is configured to translate this received rotational motion into a different form of motion. Specifically, coupler 218 may interact with pull screw 422, for instance, through a threaded engagement, whereby rotation of coupler 218 induces linear translation of pull screw 422 relative to mount 214 and coupler 218.

The interaction between stabilizing arm 106 and arm slot 212, which is shown as a feature of mount 214, serves a crucial role in maintaining alignment and preventing unwanted relative movement. When stabilizing arm 106 is engaged within arm slot 212, rotational movement between outer sleeve 104 (to which stabilizing arm 106 may be affixed or integral) and mount 214 can be restricted. This interlock ensures that torque applied to rotary driver 102 is effectively directed to coupler 218 and pull screw 422, rather than causing unintended pivoting or rotation of the entire handle assembly relative to mount 214 or an associated implant.

FIGS. 4A and 4B appear to illustrate two different states of connection mechanism 420, primarily showing a change in the axial position of pull screw 422 relative to coupler 218 and mount 214. In FIG. 4A, pull screw 422 is shown in a more extended position, while in FIG. 4B, pull screw 422 is depicted in a more retracted position. This change in position of pull screw 422 is indicative of the linear actuation achieved through the rotational input to rotary driver 102 and the subsequent interaction between coupler 218 and pull screw 422. Such linear movement of pull screw 422 may be utilized to actuate features of an implant, effect a connection, or apply tension.

—FIG. 5—

Figure 5:
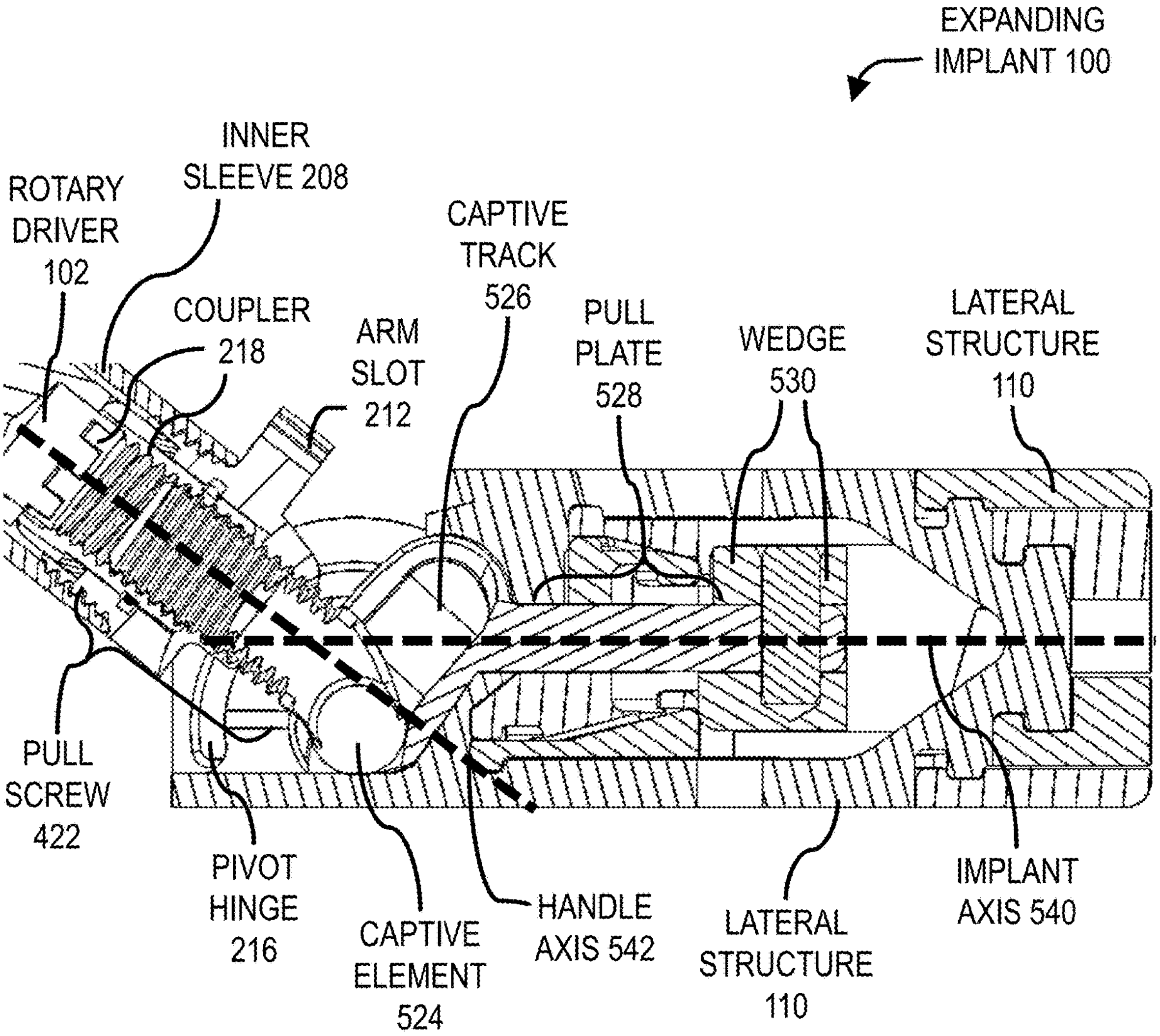
FIG. 5 is a diagram of a cutaway view of an expanding implant.

FIG. 5 is a diagram of a cutaway view of an expanding implant.

Captive element 524 is a distinct feature or an integrated portion of pull screw 422, which is configured to engage with and be constrained by captive track 526. In one or more embodiments, captive element 524 may be formed with a spherical, oblong, protruding, or any other suitable shape or geometry. This configuration is selected so that captive element 524 is retained within captive track 526, whereby constrained movement can be ensured. As a non-limiting example, captive element 524 may take the form of a pin riding within a defined path of captive track 526. While captive element 524 may be permitted to pivot or rotate freely within the confines of captive track 526, its translational movement is generally restricted to a path defined by captive track 526.

Captive track 526 is a component of expanding implant 100 which is a guiding channel or pathway which is configured to largely surround captive element 524 and to thereby constrain movement of captive element 524. In one or more embodiments, captive track 526 may be attached to, or integrally formed with, pull plate 528. Due to this connection, any movement experienced by captive track 526, such as linear shifting, can be translated into similar or corresponding movement of pull plate 528. For instance, by means of linear displacement of captive track 526, pull plate 528 may also be caused to shift linearly. That is, input forces from pull screw 422 (via captive element 524) can be translated into controlled motion of pull plate 528 (and wedge 530 thereafter). Further, the geometry of captive track 526 is designed for guiding captive element 524 along a predetermined path and to allow for implant pivot 100P (as also constrained by pivot hinge 216). In one or more embodiments, the specific path defined by captive track 526 may allow for linear motion of pull screw 422 (in any direction permitted by implant pivot 100P) to cause linear motion of captive track 526 in fixed direction-which may not be the same linear direction pull screw 422 translated.

Pull plate 528 is a component of expanding implant 100 which is a substantially rigid structural component designed to function as a connecting element between captive track 526 and wedge 530 (and attached to both). In one or more embodiments, pull plate 528 is configured so that movements which may be experienced by captive track 526 are effectively transferred through pull plate 528 to wedge 530. Through this configuration, corresponding displacement or actuation of wedge 530 can be achieved as a result of displacement or actuation of captive track 526. Furthermore, it is contemplated that captive track 526, pull plate 528, and wedge 530 may be fabricated or formed as a single, monolithic part, through which an integrated structural unit for motion transmission may be created. In one or more embodiments, captive track 526 may be considered attached to wedge 530, as pull plate 528 may be considered as the structural element to achieve that attachment.

Wedge 530 is a component of expanding implant 100, which may include one or more inclined surfaces designed to redirect motion or force. In one or more embodiments, when translation of wedge 530 occurs in a direction towards captive element 524 of pull screw 422 (via captive track 526 and pull plate 528), interaction between the sides of wedge 530 and one or more lateral structures 110 may be effectuated. This interaction is configured such that outward shifting of said lateral structures 110 is caused. The direction of this outward shift of lateral structures 110 is generally orthogonal to the direction of translation of wedge 530, whereby expansion of expanding implant 100 can be achieved. In one or more embodiments, wedge 530 may include geometry to retract lateral structures 110 if moved in the opposite direction. Accordingly, wedge 530 may have some constrained mating surfaces (e.g., channels, tracks, lips, etc.) with lateral structures 110 to permit wedge 530 to push lateral structures 110 outward as well as pull lateral structures 110 inward.

Implant axis 540 is a theoretical line by which the central longitudinal dimension of expanding implant 100 is represented. In one or more embodiments, implant axis 540 may be understood to extend substantially along the length of expanding implant 100. The orientation of implant axis 540 can be further defined as running in a direction that may pass through captive track 526 and extend through wedge 530. Reference for description of movements, alignments, or orientations of various components within or associated with expanding implant 100, such as the direction of translation of wedge 530 or general alignment for insertion of expanding implant 100, may be provided by this implant axis.

Handle axis 542 is a theoretical line by which the central longitudinal extent of handle 101 is defined. In one or more embodiments, handle axis 542 may be understood to run along the overall length of handle 101. This axis is typically oriented in a direction corresponding to the center line of coaxially nested components that may be included in handle 101, such as outer sleeve 104, inner sleeve 208, and rotary driver 102. Reference for description of the alignment of handle 101, or for definition of the relationship between handle 101 and other interconnected parts like expanding implant 100, may be provided by handle axis 542.

—FIGS. 6A-6B—

Figure 6A:
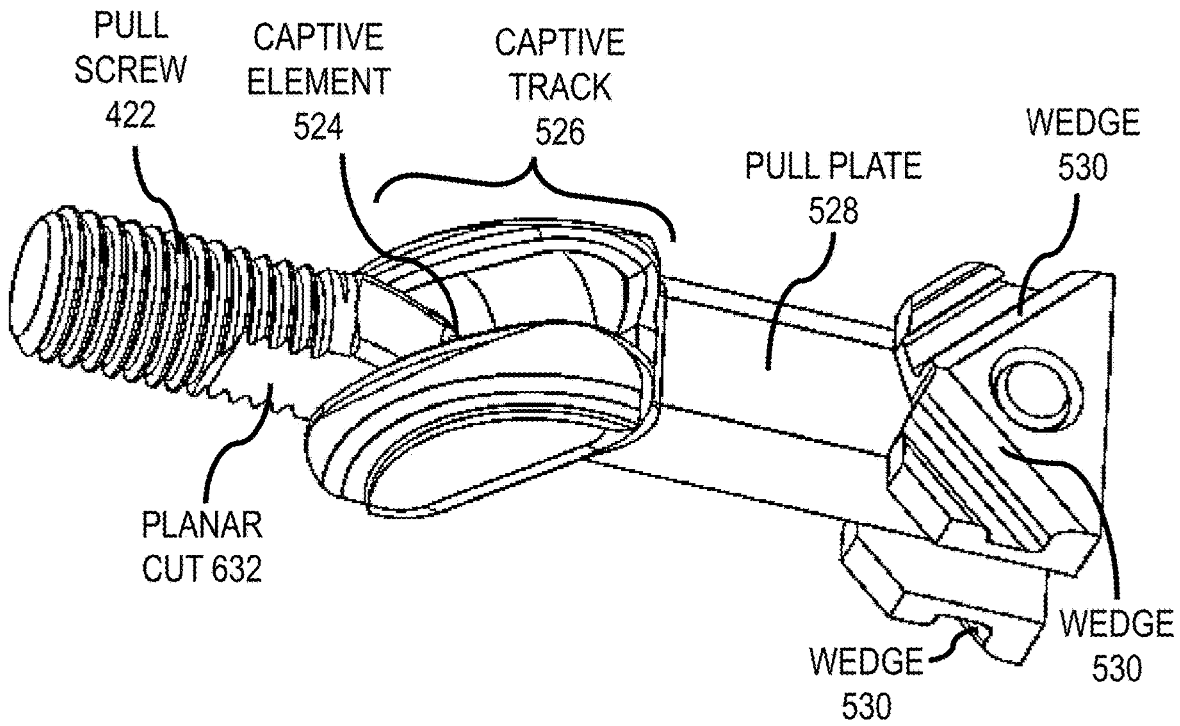
FIG. 6A is a diagram of some of the components of an expanding implant.
Figure 6B:
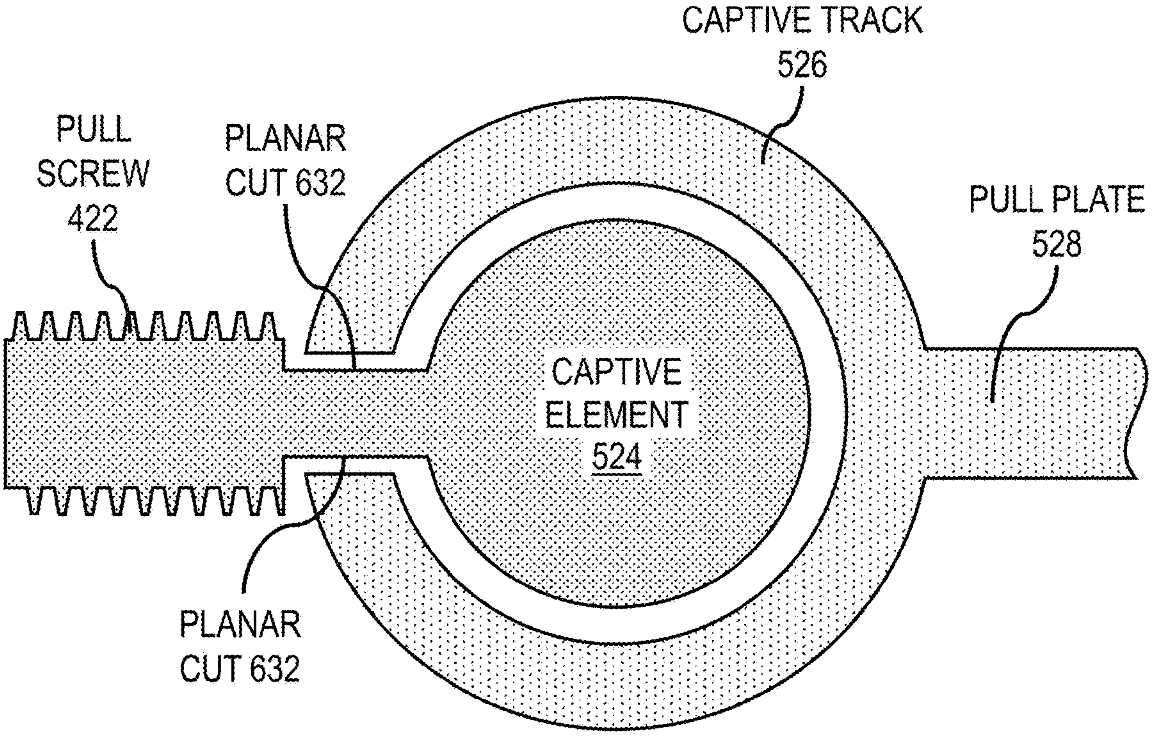
FIG. 6B is a diagram of a closeup view of the pull screw and captive track of an expanding implant.

FIG. 6A is a diagram of some of the components of an expanding implant. FIG. 6B is a diagram of a closeup view of the pull screw and captive track of an expanding implant.

Planar cut 632 is a machined flat surface feature which is formed on one or more side portions of pull screw 422. In one or more embodiments, as a result of the presence of one or more such planar cuts 632, a region of reduced width may be formed on pull screw 422; for example, this region may be located between a circular threaded portion of pull screw 422 and captive element 524. This narrowed region is typically the section of pull screw 422 disposed across an opening in captive track 526 (i.e., a "captive track opening"). Due to this specific geometry, rotation of pull screw 422 can be restricted or prevented by one or more planar cuts 632, as the opening in captive track 526 may not be dimensioned to accommodate the full, uncut diameter of pull screw 422.

—FIGS. 7A-7B—

Figure 7A:
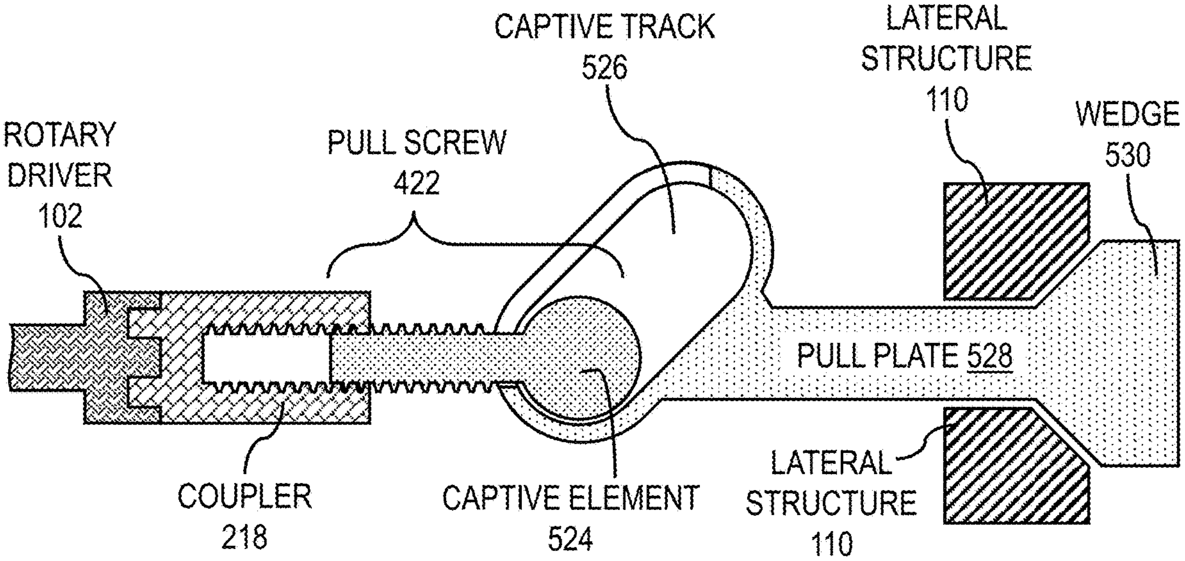
FIG. 7A is a diagram showing a pull screw parallel to pull plate, before expansion.
Figure 7B:
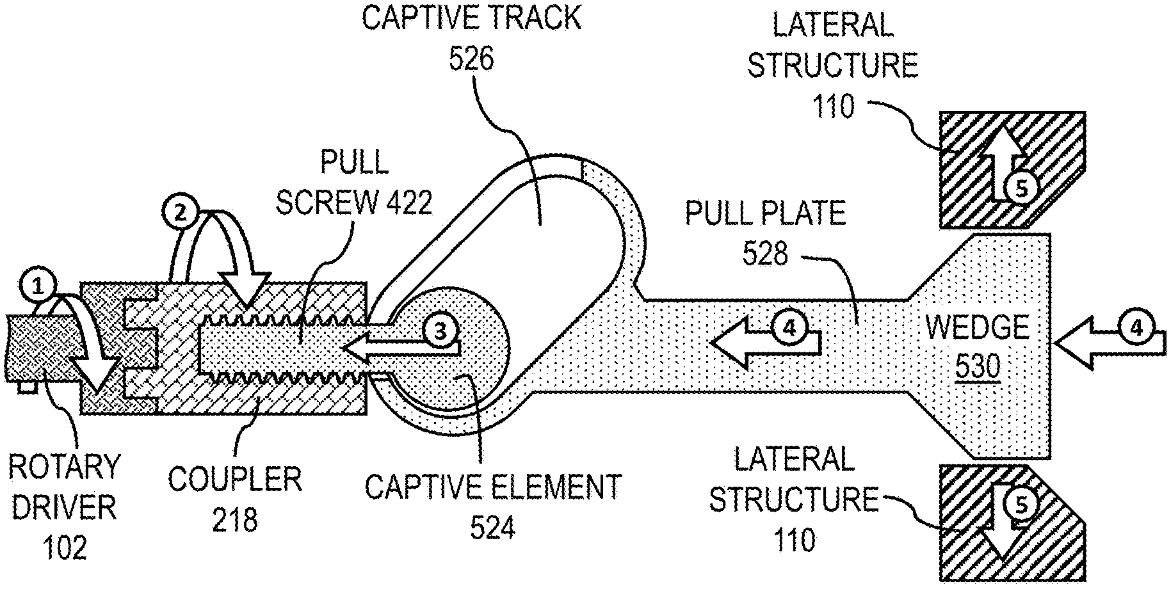
FIG. 7B is a diagram showing a pull screw parallel to pull plate, after expansion.

FIG. 7A is a diagram showing a pull screw parallel to pull plate, before expansion. FIG. 7B is a diagram showing a pull screw parallel to pull plate, after expansion.

For simplicity, in the example of FIGS. 7A-7B, wedge 530 and lateral structures 110 are depicted extending outward in the same plane in which the other components reside. However, one of ordinary skill in the art, provided the benefit of this detailed description, would understand that wedge 530 and lateral structures 110 may extend outward in a directional orthogonal to this plane, as configured in FIGS. 1F, 1G, 2D, and the descriptions thereof.

As depicted in FIG. 7A, pull screw 422 is only partially threaded into coupler 218 and lateral structures 110 are not extended outward and remain closer to the pull plate 528. Whereas, as depicted in FIG. 7B pull screw 422 is more fully threaded into coupler 218 and lateral structures 110 extend outward and away from pull plate 528.

In one or more embodiments, the components depicted in FIG. 7A may rotate and translate to the positions depicted in FIG. 7B, by the series of motions described below (labeled in FIG. 7B). For ease of comparison across FIGS. 7A-7B, rotary driver 102 and coupler 218 remain in the same position (they do not translate but may rotate).

At (1), rotary driver 102 undergoes driver rotation 102R (e.g., by a human user and/or controlled machine).

At (2), coupler 218 rotates with rotary driver 102 due to the interlocking of rotary driver 102 with coupler 218.

At (3), pull screw 422 is threaded into coupler 218, but unable to rotate (i.e., due to the geometry of planar cuts 632 and captive track 526 (see FIG. 6B)). Consequently, pull screw 422 translates further into the threads of coupler 218.

At (4), due to the geometry of captive element 524 (of pull screw 422) within captive track 526, the translation of captive element 524 forces the translation of captive track 526, pull plate 528, and wedge 530.

Further, at (4), the linear direction of pull screw 422 is parallel to the constrained linear direction of pull plate 528. Accordingly, there may be minimal relative movement of captive element 524 with respect to captive track 526.

At (5), as wedge 530 translates, the ramped surfaces of wedge 530 force lateral structures 110 to undergo lateral movement 110M and move outward (in a direction away from pull plate 528).

—FIGS. 8A-8B—

Figure 8A:
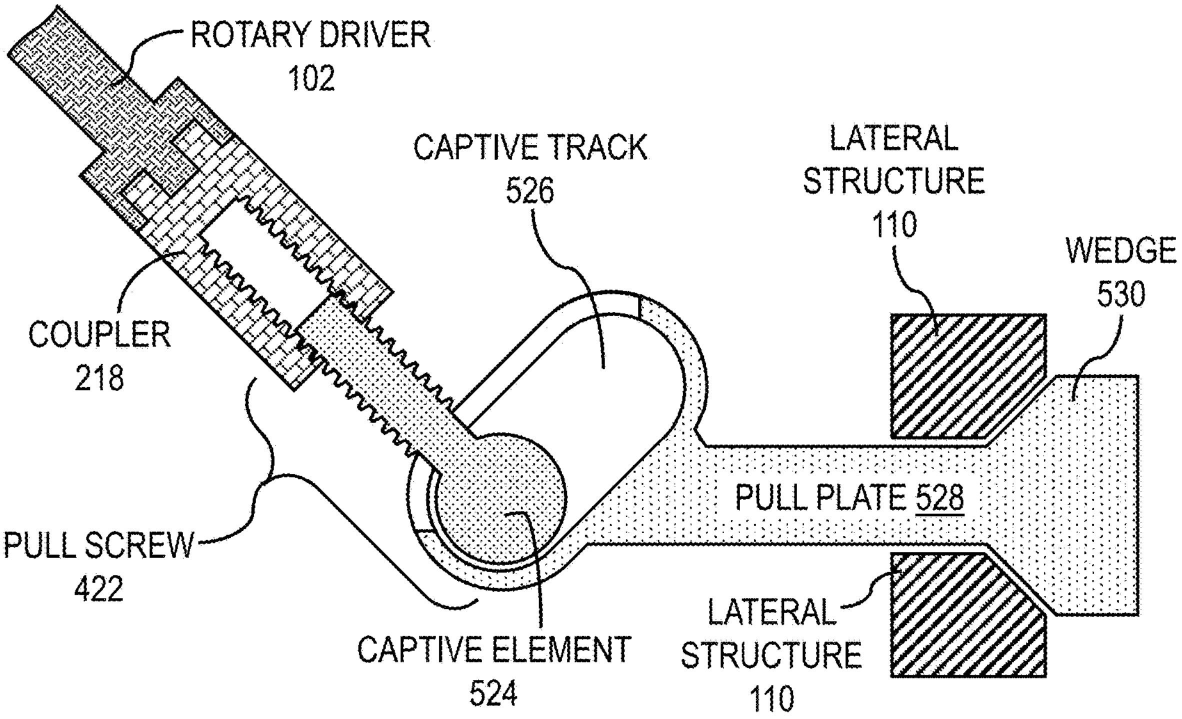
FIG. 8A is a diagram showing a pull screw at a 45° angle to pull plate, before expansion.
Figure 8B:
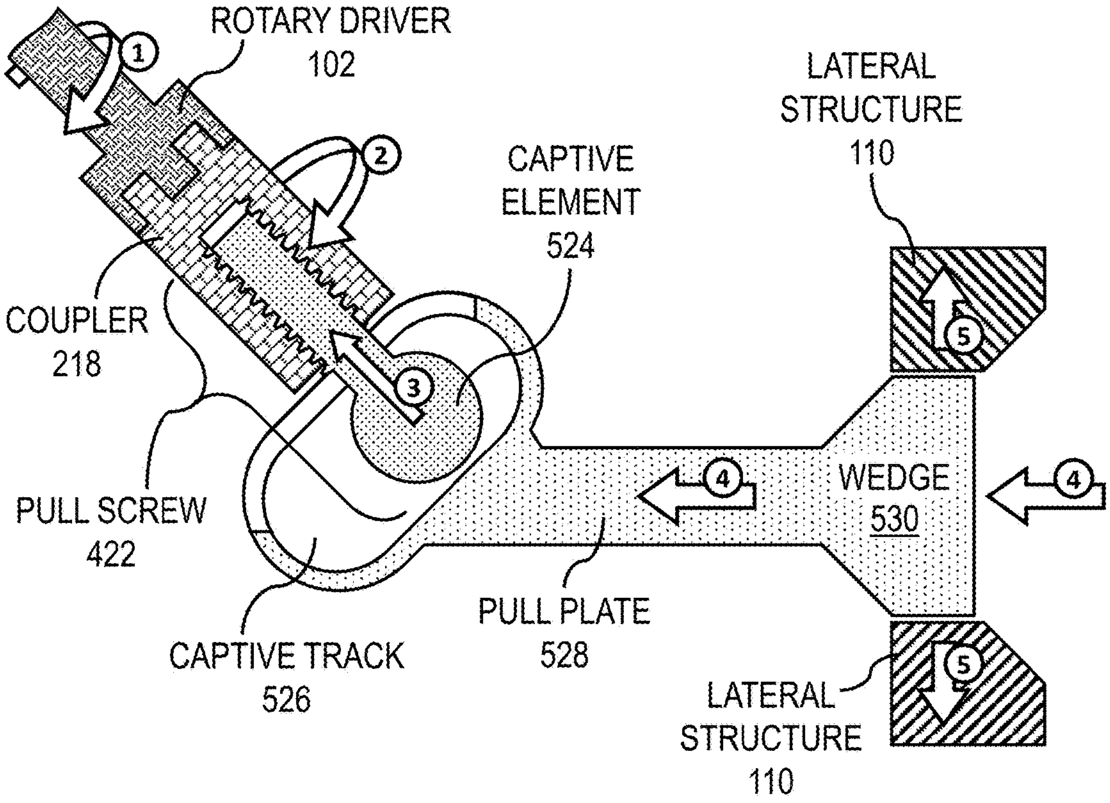
FIG. 8B is a diagram showing a pull screw at a 45° angle to pull plate, after expansion.

FIG. 8A is a diagram showing a pull screw at a 45° angle to pull plate, before expansion. FIG. 8B is a diagram showing a pull screw at a 45° angle to pull plate, after expansion.

For simplicity, similar to the depiction in FIGS. 7A-7B, in the example of FIGS. 8A-8B, wedge 530 and lateral structures 110 are depicted extending outward in the same plane in which the other components reside. Further, as depicted in FIG. 8A, pull screw 422 is only partially threaded into coupler 218 and lateral structures 110 are not extended outward and remain closer to the pull plate 528. Whereas, as depicted in FIG. 8B, pull screw 422 is more fully threaded into coupler 218 and lateral structures 110 extend outward and away from pull plate 528.

In one or more embodiments, the components depicted in FIG. 8A may rotate and translate to the positions depicted in FIG. 8B by the series of motions described below (labeled in FIG. 8B). For ease of comparison across FIGS. 8A-8B, rotary driver 102 and coupler 218 remain in the same position (they do not translate but may rotate).

At (1), rotary driver 102 undergoes driver rotation 102R (e.g., by a human user and/or controlled machine).

At (2), coupler 218 rotates with rotary driver 102 due to the interlocking of rotary driver 102 with coupler 218.

At (3), pull screw 422 is threaded into coupler 218, but unable to rotate (i.e., due to the geometry of planar cuts 632 and captive track 526 (see FIG. 6B)). Consequently, pull screw 422 translates further into the threads of coupler 218.

At (4), due to the geometry of captive element 524 (of pull screw 422) within captive track 526, the translation of captive element 524 forces the translation of captive track 526, pull plate 528, and wedge 530.

Further, at (4), the direction of pull screw 422 is angled with respect to the constrained linear direction of pull plate 528 (45° from parallel). Accordingly, in order for captive element 524 to maintain the same linear direction, captive element 524 moves along the contours of captive track 526. In turn, due to this permissible geometry, captive element 524 is able to continue to force linear motion of captive track 526, pull plate 528, and wedge 530 (in one or more embodiments, captive track 526 may be considered to move around captive element 524).

At (5), as wedge 530 translates, the ramped surfaces of wedge 530 force lateral structures 110 to undergo lateral movement 110M and move outward (in a direction away from pull plate 528).

—FIGS. 9A-9B—

Figure 9A:
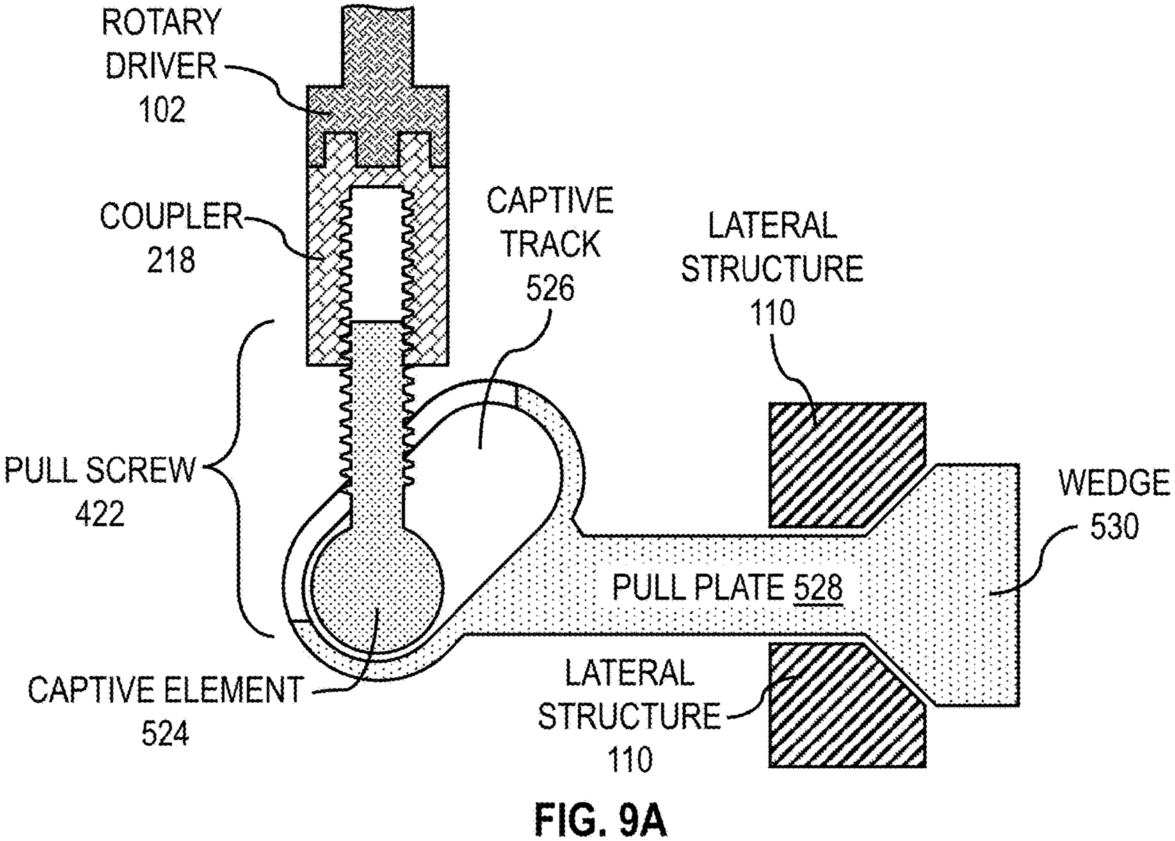
FIG. 9A is a diagram showing a pull screw at a right angle to pull plate, before expansion.
Figure 9B:
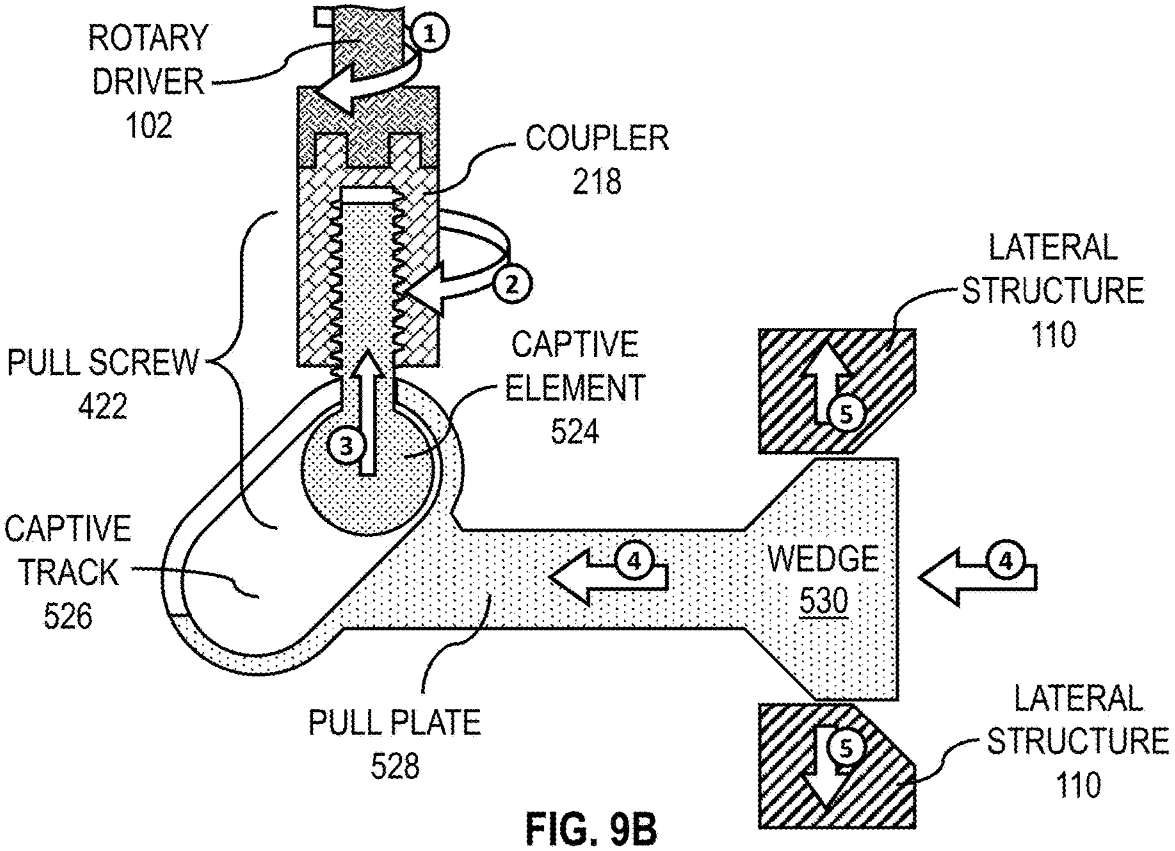
FIG. 9B is a diagram showing a pull screw at a right angle to pull plate, after expansion.

FIG. 9A is a diagram showing a pull screw at a right angle to pull plate, before expansion. FIG. 9B is a diagram showing a pull screw at a right angle to pull plate, after expansion.

For simplicity, similar to the depiction in FIGS. 7A-7B and FIGS. 8A-8B, in the example of FIGS. 9A-9B, wedge 530 and lateral structures 110 are depicted extending outward in the same plane in which the other components reside. Further, as depicted in FIG. 9A, pull screw 422 is only partially threaded into coupler 218 and lateral structures 110 are not extended outward and remain closer to the pull plate 528. Whereas, as depicted in FIG. 9B, pull screw 422 is more fully threaded into coupler 218 and lateral structures 110 extend outward and away from pull plate 528.

In one or more embodiments, the components depicted in FIG. 9A may rotate and translate to the positions depicted in FIG. 9B by the series of motions described below (labeled in FIG. 9B). For ease of comparison across FIGS. 9A-9B, rotary driver 102 and coupler 218 remain in the same position (they do not translate but may rotate).

At (1), rotary driver 102 undergoes driver rotation 102R (e.g., by a human user and/or controlled machine).

At (2), coupler 218 rotates with rotary driver 102 due to the interlocking of rotary driver 102 with coupler 218.

At (3), pull screw 422 is threaded into coupler 218, but unable to rotate (i.e., due to the geometry of planar cuts 632 and captive track 526 (see FIG. 6B)). Consequently, pull screw 422 translates further into the threads of coupler 218.

At (4), due to the geometry of captive element 524 (of pull screw 422) within captive track 526, the translation of captive element 524 forces the translation of captive track 526, pull plate 528, and wedge 530.

Further, at (4), the direction of pull screw 422 is angled with respect to the constrained linear direction of pull plate 528 (90° from parallel). Accordingly, in order for captive element 524 to maintain the same linear direction, captive element 524 moves along the contours of captive track 526. In turn, due to this permissible geometry, captive element 524 is able to continue to force linear motion of captive track 526, pull plate 528, and wedge 530 (in one or more embodiments, captive track 526 may be considered to move around captive element 524).

At (5), as wedge 530 translates, the ramped surfaces of wedge 530 force lateral structures 110 to undergo lateral movement 110M and move outward (in a direction away from pull plate 528).

—FIGS. 10A-10C and 11A-11C—

Figure 10A:
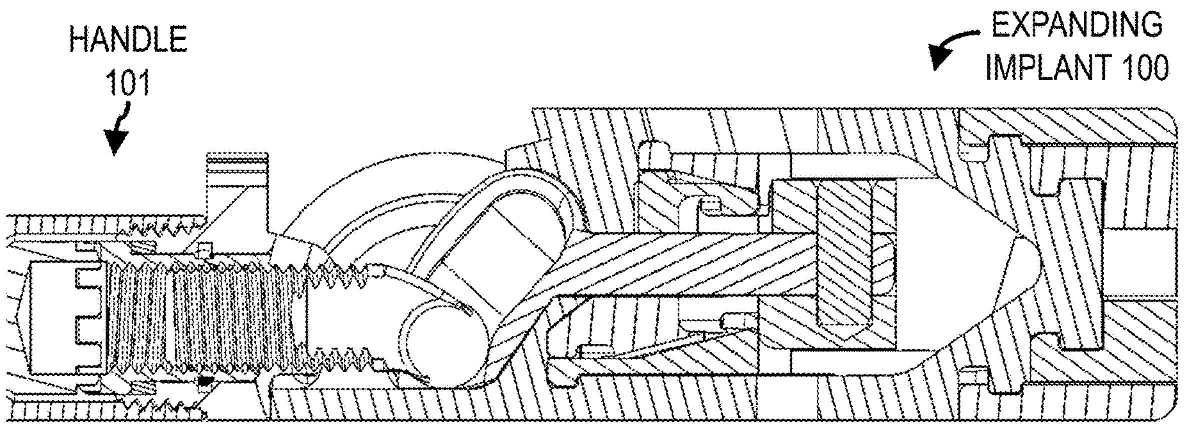
FIG. 10A is a cutaway diagram of an expanding implant, parallel with respect to the handle, before expansion.
Figure 10B:
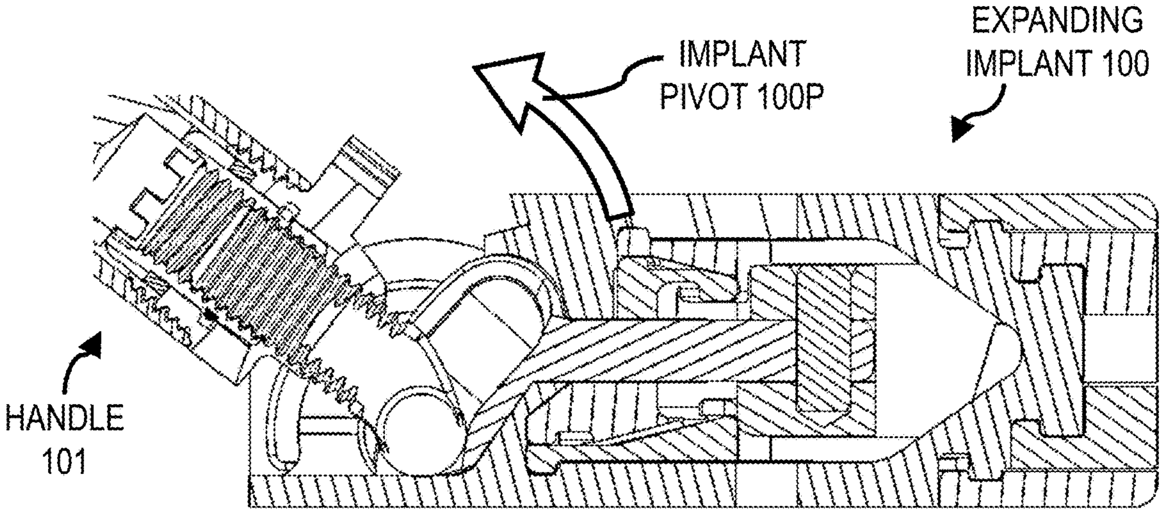
FIG. 10B is a cutaway diagram of an expanding implant, at a partial angle with respect to the handle, before expansion.
Figure 10C:
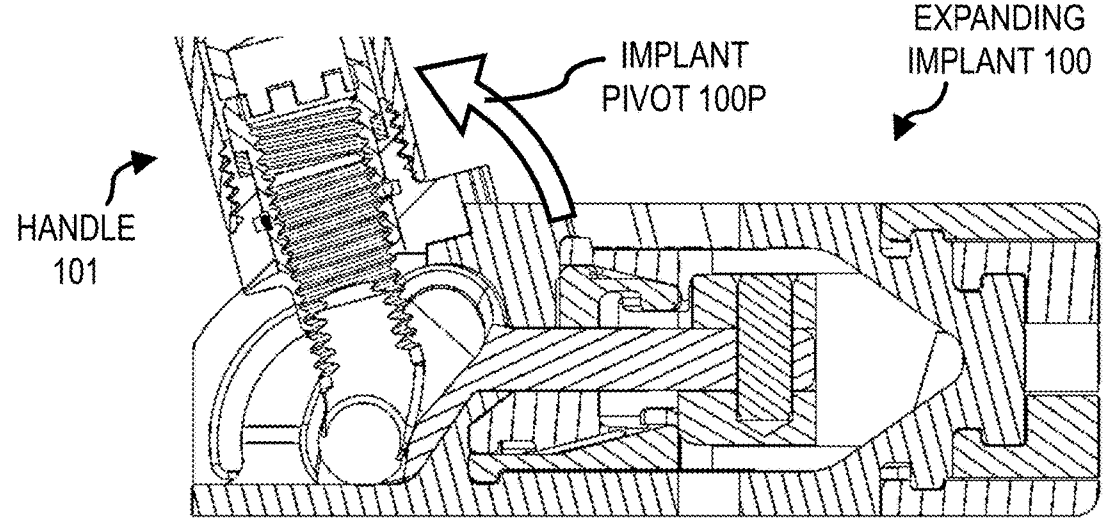
FIG. 10C is a cutaway diagram of an expanding implant, at a large angle with respect to the handle, before expansion.

FIG. 10A is a cutaway diagram of an expanding implant, parallel with respect to the handle, before expansion. FIG. 10B is a cutaway diagram of an expanding implant, at a partial angle with respect to the handle, before expansion. FIG. 10C is a cutaway diagram of an expanding implant, at a large angle with respect to the handle, before expansion.

Figure 11A:
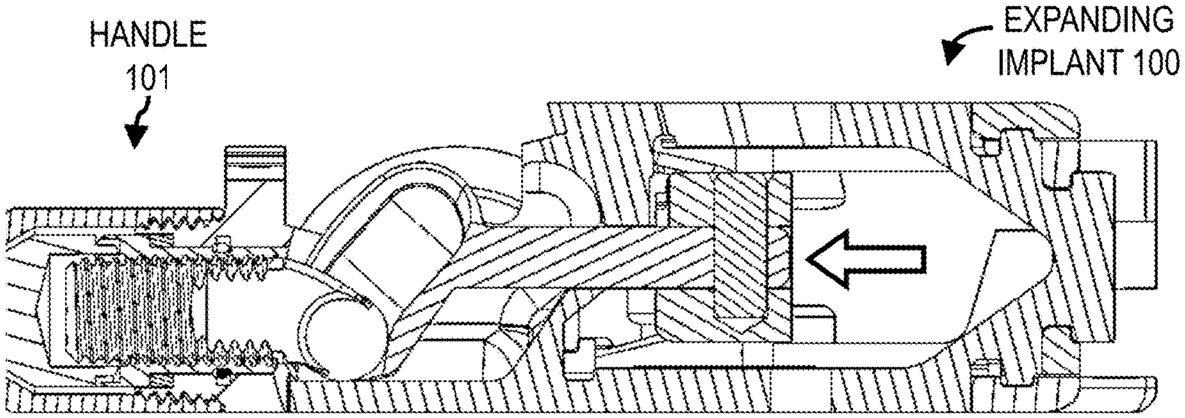
FIG. 11A is a cutaway diagram of an expanding implant, parallel with respect to the handle, after expansion.
Figure 11B:
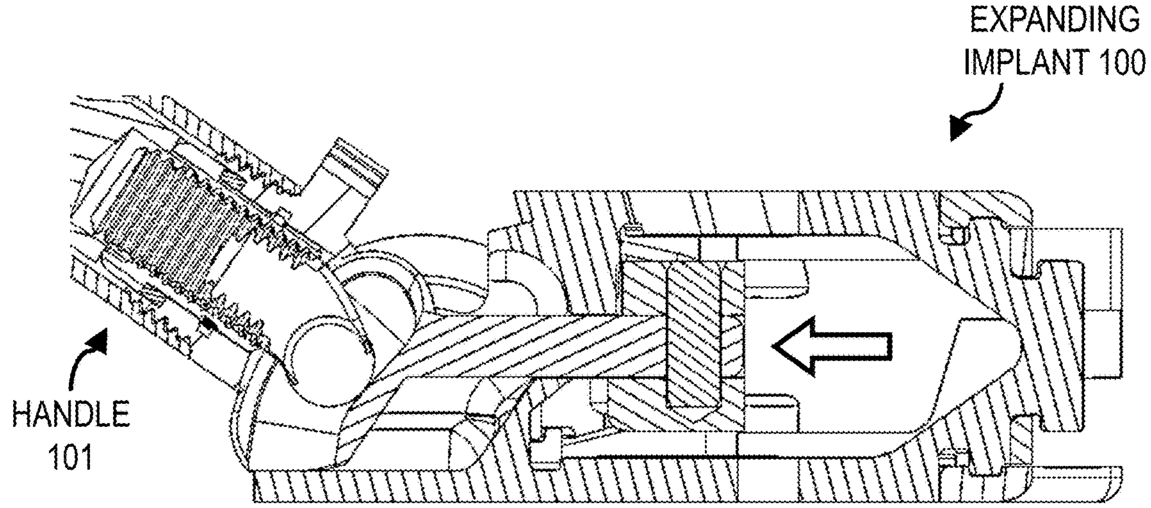
FIG. 11B is a cutaway diagram of an expanding implant, at a partial angle with respect to the handle, after expansion.
Figure 11C:
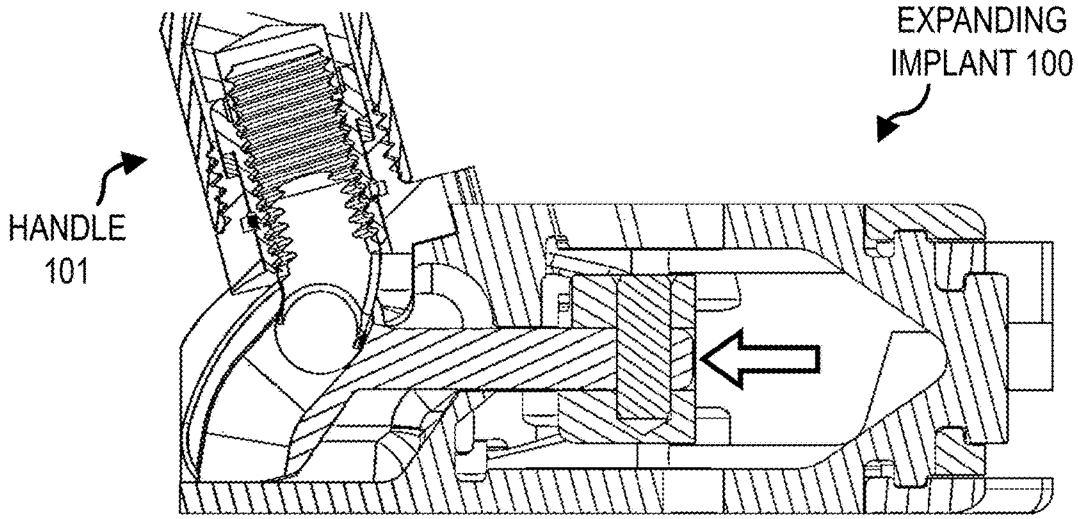
FIG. 11C is a cutaway diagram of an expanding implant, at a large angle with respect to the handle, after expansion.

FIG. 11A is a cutaway diagram of an expanding implant, parallel with respect to the handle, after expansion. FIG. 11B is a cutaway diagram of an expanding implant, at a partial angle with respect to the handle, after expansion. FIG. 11C is a cutaway diagram of an expanding implant, at a large angle with respect to the handle, after expansion.

Across FIGS. 10A-10C and FIGS. 11A-11C, handle 101 appears to rotate (clockwise) while expanding implant 100 remains stationary. However, conceptually, expanding implant 100 is described as undergoing implant pivot 100P (counterclockwise), while handle 101 remains fixed.

Each of FIGS. 10A-10C shows an expanding implant 100 and handle 101 prior to expansion of lateral structures 110, corresponding with FIGS. 11A-11C, respectively, showing expanding implant 100 after expansion of lateral structures 110.

General Notes

As it is impracticable to disclose every conceivable embodiment of the technology described herein, the figures, examples, and description provided herein disclose only a limited number of potential embodiments. A person of ordinary skill in the relevant art would appreciate that any number of potential variations or modifications may be made to the explicitly disclosed embodiments, and that such alternative embodiments remain within the scope of the broader technology. Accordingly, the scope should be limited only by the attached claims. Further, the compositions and methods are described in terms of "comprising," "containing," or "including" various components or steps, the compositions and methods may also "consist essentially of"

or "consist of" the various components and steps. Certain technical details, known to those of ordinary skill in the relevant art, may be omitted for brevity and to avoid cluttering the description of the novel aspects.

For further brevity, descriptions of similarly named components may be omitted if a description of that similarly named component exists elsewhere in the application. Accordingly, any component described with respect to a specific figure may be equivalent to one or more similarly named components shown or described in any other figure, and each component incorporates the description of every similarly named component provided in the application (unless explicitly noted otherwise). A description of any component is to be interpreted as an optional embodiment-which may be implemented in addition to, in conjunction with, or in place of an embodiment of a similarly-named component described for any other figure.

—Lexicographical Notes—

As used herein, adjective ordinal numbers (e.g., first, second, third, etc.) are used to distinguish between elements and do not create any ordering of the elements. As an example, a "first element" is distinct from a "second element", but the "first element" may come after (or before) the "second element" in an ordering of elements. Accordingly, an order of elements exists only if ordered terminology is expressly provided (e.g., "before", "between", "after", etc.) or a type of "order" is expressly provided (e.g., "chronological", "alphabetical", "by size", etc.). Further, use of ordinal numbers does not preclude the existence of other elements. As an example, a "table with a first leg and a second leg" is any table with two or more legs (e.g., two legs, five legs, thirteen legs, etc.). A maximum quantity of elements exists only if express language is used to limit the upper bound (e.g., "two or fewer", "exactly five", "nine to twenty", etc.). Similarly, singular use of an ordinal number does not imply the existence of another element. As an example, a "first threshold" may be the only threshold and therefore does not necessitate the existence of a "second threshold".

As used herein, indefinite articles "a" and "an" mean "one or more". That is, the explicit recitation of "an" element does not preclude the existence of a second element, a third element, etc. Further, definite articles (e.g., "the", "said") mean "any one of" (the "one or more" elements) when referring to previously introduced elements. As an example, there may be "a processor", where such a recitation does not preclude the existence of any number of other processors. Further, "the processor receives data, and the processor processes data" means "any one of the one or more processors receives data" and "any one of the one or more processors processes data". It is not required that the same processor both (i) receive data and (ii) process data. Rather, each of the steps ("receive" and "process") may be performed by different processors.

What is claimed is:

1. An expanding implant for placement between two vertebrae, comprising:
- a lateral structure;
- a wedge configured to cause the lateral structure to undergo lateral movement;
- a captive track attached to the wedge;
- a pull screw, comprising:
  - a captive portion at a distal end and disposed, at least partially, within the captive track;
  - a planar cut disposed across an opening of the captive track; and

- a threaded portion extending proximally from the captive portion, wherein the threaded portion is integrally formed with the captive portion;
- a coupler threaded, at least partially, onto the threaded portion of the pull screw;
- a mount attached to the coupler, wherein the coupler is configured to rotate independently from the mount;
- an arm slot attached to the mount; and
- a pivot hinge configured to allow an implant pivot between the pull screw and the captive track, wherein the mount is configured to interlock with a handle, comprising:
  - a rotary driver configured to interlock with the coupler;
  - an outer sleeve configured to surround the rotary driver; and
  - a stabilizing arm attached to the outer sleeve and configured to traverse, at least partially, through the arm slot.

2. An expanding implant, comprising:
- a lateral structure;
- a wedge configured to cause the lateral structure to undergo lateral movement;
- a captive track attached to the wedge;
- a pull screw, comprising:
  - a captive portion at a distal end and disposed, at least partially, within the captive track
  - a threaded portion extending proximally from the captive portion, wherein the threaded portion is integrally formed with the captive portion; and
  - a pivot hinge configured to allow an implant pivot between the pull screw and the captive track, wherein the expanding implant is configured undergo the implant pivot; and after the implant pivot, permit the lateral movement of the lateral structure using the pull screw.

3. The expanding implant of claim 2, further comprising:
- a coupler threaded, at least partially, onto the threaded portion of the pull screw.

4. The expanding implant of claim 3, further comprising:
- a mount attached to the coupler, wherein the coupler is configured to:
  - rotate independently from the mount.

5. The expanding implant of claim 4, wherein the mount is configured to:
- interlock with a handle, wherein the handle comprises:
  - a rotary driver configured to interlock with the coupler.

6. The expanding implant of claim 5, wherein the rotary driver is further configured to:
- cause the lateral movement of the lateral structure.

7. The expanding implant of claim 6, wherein the rotary driver is configured to:
- cause the lateral movement by causing a rotation of the coupler.

8. The expanding implant of claim 7, wherein the coupler is further configured to:
- cause a first linear movement of the pull screw along a handle axis.

9. The expanding implant of claim 8, wherein the pull screw is further configured to:
- cause a second linear movement of the wedge along an implant axis.

10. The expanding implant of claim 9, wherein the handle axis and the implant axis are not parallel.

11. A method of operating an expanding implant, comprising:

placing the expanding implant between a first vertebra and a second vertebra using a handle attached to the expanding implant, wherein the expanding implant comprises:

a first lateral structure and a second lateral structure;

a wedge configured to cause the lateral structure to undergo lateral movement;

a captive track attached to the wedge;

a pull screw, comprising:

a captive portion at a distal end and disposed, at least partially, within the captive track;

a threaded portion extending proximally from the captive portion, wherein the threaded portion is integrally formed with the captive portion; and a pivot hinge configured to allow an implant pivot between the pull screw and the captive track, wherein the expanding implant is configured to undergo the implant pivot; and after the implant pivot, permit the lateral movement of the lateral structure using the pull screw;

causing implant pivot of the expanding implant;

causing first lateral movement of a first lateral structure of the expanding implant using a rotary driver of the handle;

causing second lateral movement of a second lateral structure of the expanding implant using the rotary driver; and removing the handle from the expanding implant.

12. The method of claim 11, wherein the first lateral structure contacts the first vertebra.

13. The method of claim 12, wherein the second lateral structure contacts the second vertebra.

14. The method of claim 11, wherein the placing the expanding implant uses a stabilizing arm attached to the handle, wherein the stabilizing arm interlocks with an arm slot on the expanding implant.

15. The method of claim 14, wherein prior to causing the implant pivot, the method further comprises:

removing the stabilizing arm from the arm slot.

16. The method of claim 15, wherein causing the implant pivot of the expanding implant comprises:

pushing the expanding implant against an anterior longitudinal ligament.

17. The method of claim 11, wherein causing the first lateral movement of the first lateral structure and causing the second lateral movement of the second lateral structure using the rotary driver comprises:

rotating the rotary driver, thereby causing a rotation of a coupler interlocked with the rotary driver;

the rotation of the coupler causing a first linear movement of pull screw threaded with the coupler;

wherein the first linear movement of the pull screw causing a second linear movement of wedge; and the second linear movement of the wedge causing the first lateral movement and the second lateral movement.

18. The method of claim 11, wherein after causing the implant pivot and prior to causing the first lateral movement, a handle axis of the handle and an implant axis of the expanding implant are not parallel.

19. The method of claim 11, wherein removing the handle from the expanding implant comprises disengaging an inner sleeve of the handle from a mount of the expanding implant; and disengaging the rotary driver from a coupler of the expanding implant.

* * * * *